United States Patent
Winters et al.

(10) Patent No.: US 7,809,427 B2
(45) Date of Patent: Oct. 5, 2010

(54) TIME DOMAIN INVERSE SCATTERING TECHNIQUES FOR USE IN MICROWAVE IMAGING

(75) Inventors: David W. Winters, Madison, WI (US); Barry D. Van Veen, McFarland, WI (US); Susan C. Hagness, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1638 days.

(21) Appl. No.: 11/056,342

(22) Filed: Feb. 11, 2005

(65) Prior Publication Data

US 2006/0241409 A1    Oct. 26, 2006

(51) Int. Cl.
*A61B 5/05* (2006.01)
(52) U.S. Cl. ..................... 600/430; 382/131
(58) Field of Classification Search ............. 600/410, 600/411, 425, 430; 324/637–646, 76.14; 343/700; 607/101
See application file for complete search history.

(56) References Cited

U.S. PATENT DOCUMENTS

| | | | |
|---|---|---|---|
| 4,805,627 | A | 2/1989 | Klingenbeck et al. |
| 5,016,018 | A | 5/1991 | Chang et al. |
| 5,363,050 | A | 11/1994 | Guo et al. |
| 5,570,691 | A | 11/1996 | Wright et al. |
| 5,704,355 | A | 1/1998 | Bridges |
| 5,706,013 | A | 1/1998 | Melvin et al. |
| 5,807,257 | A | 9/1998 | Bridges |
| 5,829,437 | A | 11/1998 | Bridges |
| 5,942,899 | A | 8/1999 | Shrekenhamer et al. |
| 5,983,124 | A | 11/1999 | Carr |
| 6,005,916 | A | 12/1999 | Johnson et al. |
| 6,061,589 | A | 5/2000 | Bridges et al. |
| 6,091,361 | A | 7/2000 | Davis et al. |
| 6,161,034 | A | 12/2000 | Burbank et al. |

(Continued)

FOREIGN PATENT DOCUMENTS

EP    0222315 A2    5/1987

(Continued)

OTHER PUBLICATIONS

International Search Report dated Dec. 15, 2006 for PCT/US2006/004533.

(Continued)

*Primary Examiner*—Brian Casler
*Assistant Examiner*—Parikha S Mehta
(74) *Attorney, Agent, or Firm*—Bell & Manning, LLC

(57) ABSTRACT

A system and a method are provided for estimating the average dielectric properties of a plurality of regions in space. The application of this technique is illustrated for determining the average properties of breast tissue. The knowledge of average properties is important when UWB microwave radar signal processing algorithms are used for tumor detection and localization. The method is an extension of a time-domain inverse scattering algorithm based on the finite-difference time-domain method. A hybrid conjugate gradient optimization is used to minimize a cost function defined between a measured and a calculated total electromagnetic field at a series of antennas. The output of the method is an average set of electromagnetic material parameters that describe specific regions of interest in either a non-dispersive heterogeneous medium or a dispersive heterogeneous medium.

29 Claims, 13 Drawing Sheets

U.S. PATENT DOCUMENTS

| | | | |
|---|---|---|---|
| 6,421,550 | B1 | 7/2002 | Bridges et al. |
| 6,448,788 | B1 | 9/2002 | Meaney et al. |
| 7,061,970 | B2 | 6/2006 | Reed et al. |
| 7,454,242 | B2 | 11/2008 | Fear et al. |
| 2002/0061280 | A1 | 5/2002 | Mattrey |
| 2002/0163480 | A1 | 11/2002 | Eiges |
| 2002/0197209 | A1 | 12/2002 | Mattrey |
| 2003/0088180 | A1 | 5/2003 | Bond et al. |
| 2004/0167399 | A1 | 8/2004 | Li |
| 2005/0251018 | A1 | 11/2005 | Gleman |
| 2005/0259621 | A1 | 11/2005 | Lee |
| 2006/0058606 | A1 | 3/2006 | Davis et al. |
| 2006/0183995 | A1 | 8/2006 | Bond et al. |
| 2007/0282200 | A1 | 12/2007 | Johnson et al. |

FOREIGN PATENT DOCUMENTS

| | | |
|---|---|---|
| WO | WO 03/003907 | 1/2003 |
| WO | WO 2004/014221 | 2/2004 |

OTHER PUBLICATIONS

No-Weon Kang, et al., "A New 2-D Image Reconstruction Algorithm Based on FDTD and Design Sensitivity Analysis," IEEE Transactions on Microwave Theory and Techniques, vol. 50, No. 12, Dec. 2002, pp. 2734-2740.

Yu-Hong Dai, "A Family of Hybrid Conjugate Gradient Methods for Unconstrained Optimization," Mathematics of Computation, vol. 72, No. 243., pp. 1317-1328, Feb. 3, 2003, American Mathematical Society.

I. T. Rekanos, "Time-Domain Inverse Scattering Using Lagrange Multipliers: An Interative FDTD-Based Optimization Technique," J. of Electromagn. Waves and Appl., 2003, pp. 271-289, vol. 27, No. 2.

Takashi Takenaka, Hui Zhou, and Toshiyuki Tanaka, "Inverse Scattering for a Three-Dimensional Object in the Time Domain", J. Opt. Soc. Am. A, vol. 20, No. 10, pp. 1867-1874, Optical Society of America, Oct. 2003.

E. J. Bond, et al., "Microwave Imaging Via Space-Time Beamforming for Early Detection of Breast Cancer," IEEE Trans. Antennas and Propagation, vol. 51, No. 8, Aug. 2003.

Li, F. et al.: "Three-Dimensional Reconstruction of Objects Buried in Layered Media Using Born and Distorted Born Iterative Methods," IEEE Geoscience and Remote Sensing Letters, IEEE Service Center, New York, NY, US, vol. 1, No. 2, Apr. 1, 2004, pp. 107-111.

Liu, Q. H. et al.: "Three-Dimensional Nonlinear Image Reconstruction for Microwave Biomedical Imaging," IEEE Transactions on Biomedical Engineering, IEEE Service Center, Piscataway, MN, US, vol. 51, No. 3, Mar. 1, 2004, pp. 544-548.

Supplementary European Search Report for European Application No. 06734641.1 dated Jun. 5, 2009.

Supplementary European Search Report for European Application No. 06719588.3 dated Jun. 17, 2009.

A Notice of Allowance issued in U.S. Appl. No. 11/340,214 mailed Jul. 9, 2009.

Hagness, Susan C. et al., "Three-Dimensional FDTD Analysis of a Pulsed Microwave Confocal System for Breast Cancer Detection: Design of an Antenna-Array Element", IEEE Transactions on Antennas and Propagation, May 1999, vol. 47, No. 5, pp. 783-791.

Supplementary European Search Report issued for EPO Patent Appl. No. 02749822.9, dated Feb. 8, 2010.

The Office Action issued in European Patent Application No. 06734641.1-2319 dated Sep. 14, 2009.

TIME DOMAIN INVERSE SCATTERING TECHNIQUES FOR USE IN MICROWAVE IMAGING

REFERENCE TO GOVERNMENT RIGHTS

This invention was made with United States government support awarded by the following agencies: NIH CA092188. The United States government has certain rights in this invention.

FIELD OF THE INVENTION

The present invention pertains generally to the field of imaging and, more particularly, to medical imaging signal processing techniques to detect and to locate tumors in tissue.

BACKGROUND OF THE INVENTION

Various imaging techniques have been employed for detecting and locating cancerous tumors in body tissue. For example, X-ray and ultrasound imaging techniques are commonly utilized in screening for breast cancer. X-ray mammography is the most effective current method for detecting early stage breast cancer. X-ray mammography, however, suffers from relatively high false positive and false negative rates, requires painful breast compression, and exposes the patient to low levels of ionizing radiation. Microwave based imaging methods have been proposed for use in imaging of breast tissue and other body tissues as an alternative to current ultrasound and X-ray imaging techniques. Microwave imaging does not require breast compression, does not expose the patient to ionizing radiation, and can be applied at low power levels. Microwave-based imaging, such as microwave tomography and radar imaging, exploits the dielectric properties contrast between normal and malignant tissue.

As an example, recent theoretical and experimental laboratory research has established the feasibility of ultrawideband (UWB) microwave radar imaging for early stage breast cancer detection. UWB microwave radar imaging is based on transmitting short-duration microwave signals into the breast using an array of antennas placed near the breast surface and then measuring the scattered microwave signals. Scattering arises due to the significant contrast in the dielectric properties that exists at microwave frequencies between normal fatty and malignant breast tissue. The temporal and spectral characteristics of the measured scattered signals are used by UWB microwave radar imaging algorithms to identify the presence and location of malignant lesions.

UWB radar signal processing algorithms for detecting and imaging breast lesions typically assume a propagation model for a homogeneous breast medium. The actual scatter, however, is acquired from heterogeneous breast tissue. Numerical and experimental laboratory studies have shown that more accurate tumor localization is achieved when the material parameters in the propagation model represent the spatial average of the properties of the actual, heterogeneous breast tissue. The average properties, however, are unknown a priori and are expected to vary from patient to patient. As a result, a calibration step that yields estimates of the patient-specific breast tissue averages is a key component of a UWB microwave radar imaging system.

Techniques have been developed for estimating the dielectric and conductive distributions in a region of space using measurements of the scattered microwave signals. The estimation problem, however, is typically nonlinear and ill-posed. Iterative inverse scattering algorithms that sequentially update the estimated spatial distributions have been employed to obtain a voxelized approximation of the actual spatial distribution of electromagnetic material properties after a sufficient number of iterations. The ill-posedness of this problem increases as the resolution of the reconstructed profile increases because the number of unknowns increases. The nonlinearity and ill-posedness of the inverse problem also tend to increase as the frequency of the probing excitation increases. Thus, what is needed is a system and a method for estimating average properties that does not suffer from the nonlinearity and ill-posedness of the full inverse scattering problem. Ideally, this system and a method are robust to various levels of knowledge of the properties of the skin layer surrounding the underlying breast tissue.

SUMMARY OF THE INVENTION

An exemplary embodiment of the invention relates to a system, a method, and at least one computer readable medium to estimate the average dielectric properties of a plurality of regions in space. The knowledge of average properties is important when UWB microwave radar signal processing algorithms are used for tumor detection and localization because previous numerical and experimental laboratory studies have shown that accurate tumor localization is achieved when the electromagnetic material parameters in the propagation model represent the spatial average of the electromagnetic material parameters of the actual, heterogeneous breast tissue. The method provided is an extension of a time-domain inverse scattering technique based on a finite-difference time-domain method. A hybrid conjugate gradient optimization is used to minimize a cost function between the measured and calculated total field at a series of antennas.

In applying the time-domain inverse scattering technique, the target object to image is divided into a plurality of regions. The output of the time domain inverse scattering technique is an average set of electromagnetic material parameters in either non-dispersive heterogeneous medium or dispersive heterogeneous medium for each of the plurality of regions. For example, the breast can be separated into two distinct medium: a skin layer (approximately homogeneous) and an underlying homogeneous breast tissue region. The two-medium geometry is sufficient to provide a clinical calibration step for a breast imaging system. Because the number of unknowns is reduced based on calculating a set of average electromagnetic material parameters for a relatively small number of regions, this inverse scattering problem is not as ill-posed as those typically encountered in other microwave tomography or radar imaging problems that rely upon solutions to the full inverse scattering problem containing numerous unknowns.

The time domain inverse scattering technique can be applied to multiple defined pluralities of regions. For example, the exact thickness of the skin layer is unknown a priori. As a result, the plurality of regions may be defined assuming different skin thicknesses that change the spatial location of each region. Comparison of the cost function generated for each of the plurality of regions identifies the "best estimate" for the skin thickness, and as a result, the "best estimate" for the average electromagnetic material parameters. Example simulation results show that the average properties estimation algorithm provided significantly better detection performance than that provided with reasonable, but incorrect guessing.

Other principal features and advantages of the invention will become apparent to those skilled in the art upon review of the following drawings, the detailed description, and the appended claims.

BRIEF DESCRIPTION OF THE DRAWINGS

The preferred embodiments will hereafter be described with reference to the accompanying drawings, wherein like numerals will denote like elements.

DETAILED DESCRIPTION OF THE EXEMPLARY EMBODIMENTS

Breast carcinomas act as significant microwave scatterers due to their large dielectric-properties contrast with the surrounding tissue. Data in published literature suggest that the malignant-to-normal breast tissue contrast in dielectric constant, and conductivity, is between 2:1 and 10:1, depending on the density of the normal tissue. The higher dielectric properties of malignant breast tissue arise, in part, from increased protein hydration and a breakdown of cell membranes due to necrosis. The contrast ratio does not vary significantly with tumor age, which suggests the potential for detecting tumors at the earliest stages of development. Preliminary measurements suggest that the contrast between the dielectric properties of normal breast tissue and some benign lesions is negligible, in which case benign lesions would not act as strong microwave scatterers, allowing discrimination of benign and cancerous lesions.

Microwaves offer exceptionally high contrast compared to other imaging modalities, such as X-ray mammography, which exploit intrinsic contrasts on the order of a few percent. Measurements suggest typical attenuation of microwave signals is less than 4 dB/cm up through 10 GHz, indicating that commercial microwave instrumentation with 100 dB of dynamic range is capable of imaging through 25 cm of tissue. In an exemplary embodiment, microwave pulses on the order of 100 ps in duration with peak powers on the order of a few milliwatts, approximately 1/100th of the power of a typical cellular phone, can be used. Assuming a pulse repetition frequency of 1 MHz and a maximum scan depth of 10 cm, an array of 100 antennas can be sequentially scanned in 0.1 seconds.

The goal of conventional microwave tomography is the recovery of the dielectric-properties profile of an object from measurement of the transmission and scattering of microwave energy through the object. In contrast, microwave radar imaging identifies the presence and the location of strong scatterers in the breast by directly imaging the scattered signal power. The use of an antenna array and short pulses enables focusing in both space and time. Thus, such a system significantly enhances the response from malignant lesions while minimizing clutter signals, thereby overcoming challenges presented by breast heterogeneity and enabling the detection of lesions as small as 1-2 mm.

Figure 1:
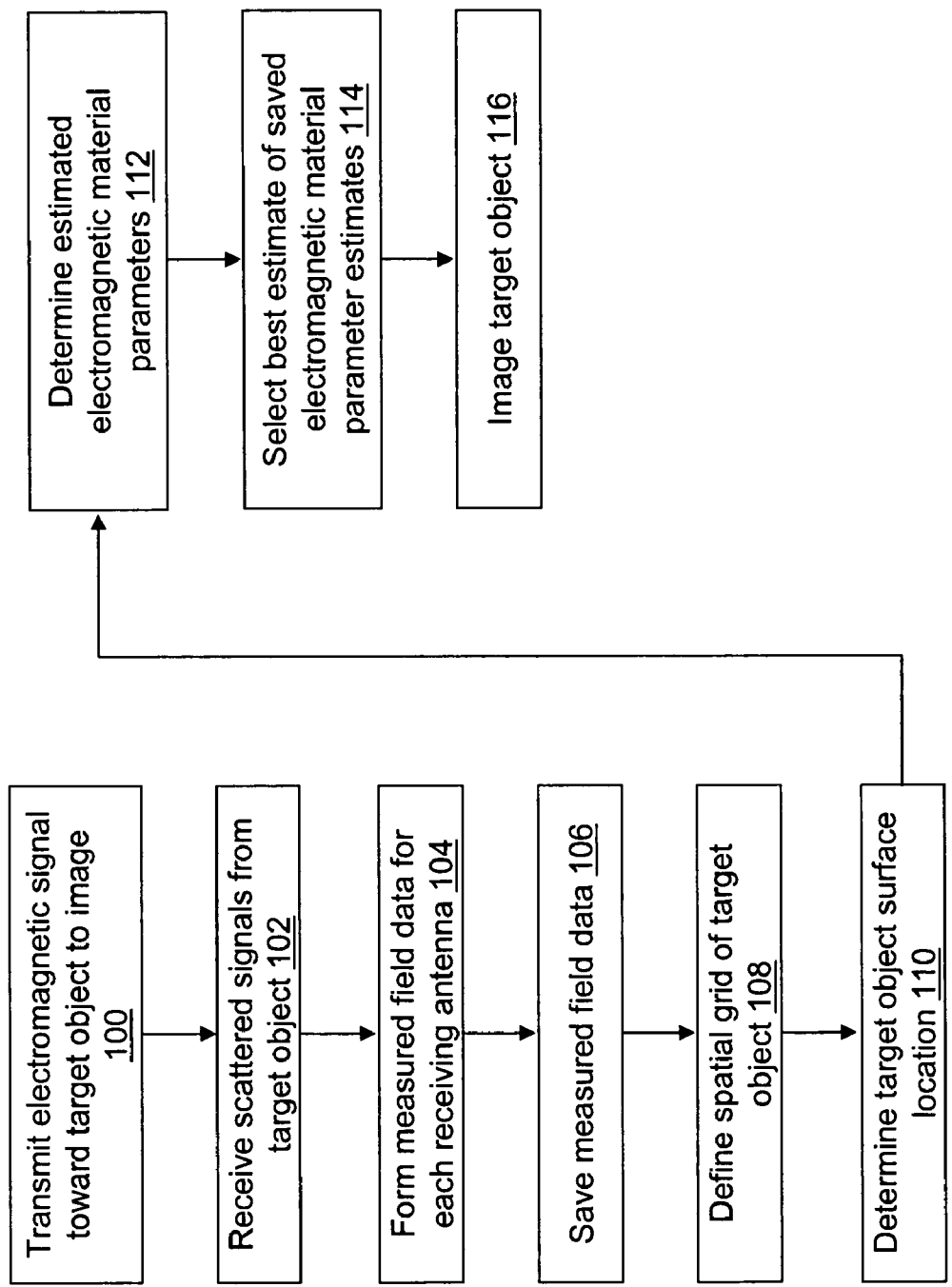
FIG. 1 is a flow diagram illustrating exemplary operations of a microwave imaging system in accordance with the invention.

With reference to FIG. 1, exemplary operations in a microwave imaging system are shown. In an operation 100, an electromagnetic signal f(t) is transmitted from a plurality of antennas that form an antenna array toward a target object to image, i.e. a breast. In an operation 102, scattered signals from the transmitted electromagnetic signal are received at the plurality of antennas. In an exemplary embodiment, one antenna of the array of antennas transmits the electromagnetic signal that is received by the remaining antennas after propagation through the object being imaged. The position of the transmitting antenna is changed and the process is repeated.

Figure 2:
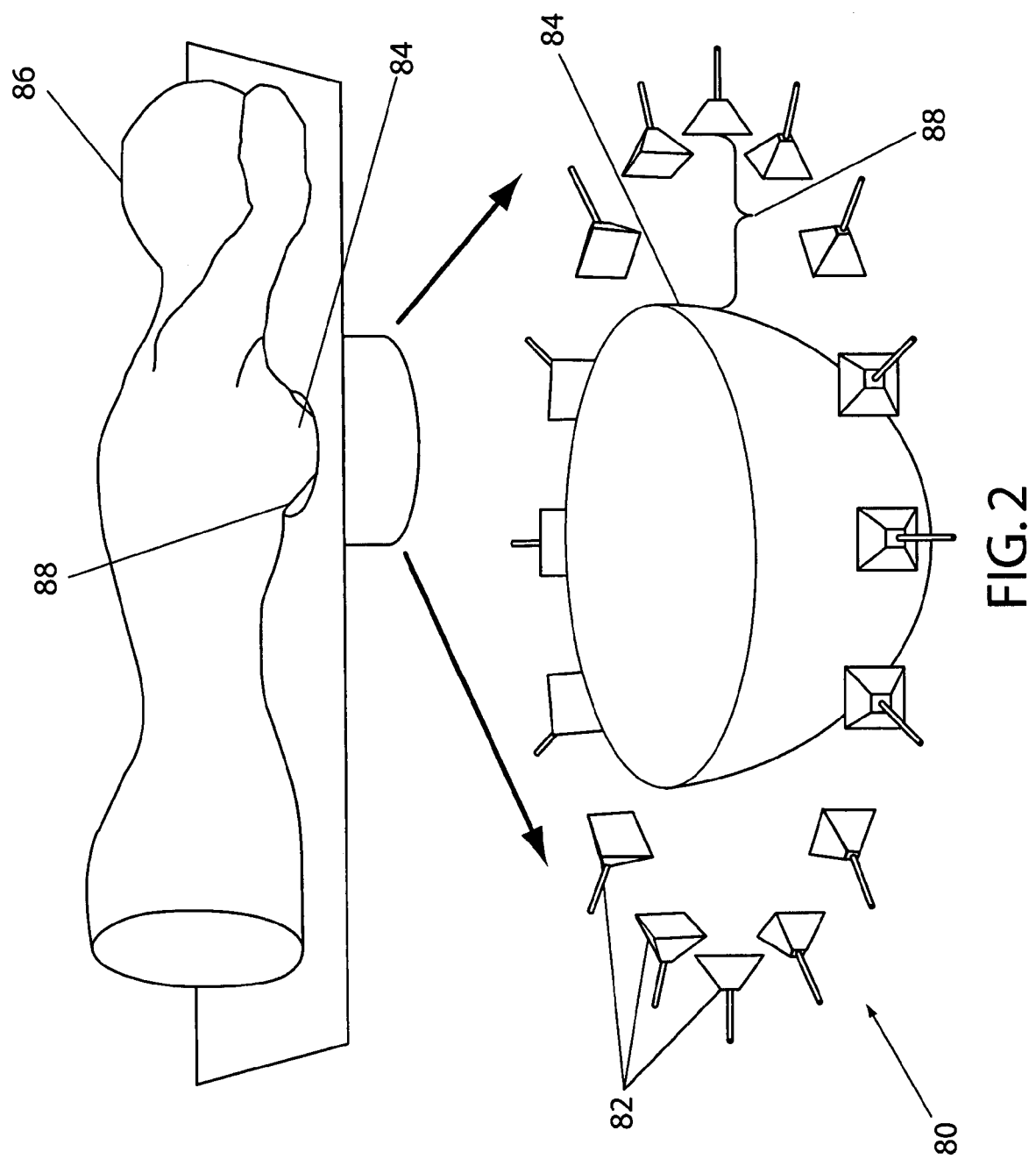
FIG. 2 is an illustrative view of an antenna array and its utilization in the microwave imaging system of the invention.

With reference to FIG. 2, an exemplary antenna array device which may be utilized in the microwave imaging system is shown generally at 80 and includes multiple individual antennas 82 arranged in a circular array at known locations relative to each other. The individual antenna elements 82 may have the "horn" shape as shown or other shapes as desired. For purposes of illustration, the antenna array device 80 is shown in FIG. 2 placed adjacent to the breast 84. The patient 86 lies face down so that the pendulous breast is encircled by the antenna array 80. The array may be scanned vertically through different coronal places of the pendulous breast to synthesize a full three-dimensional (3-D) array or the antenna array may comprise multiple rows of antennas surrounding the breast. An impedance matching liquid may be placed in the interface 88 between the antenna array 80 and the breast 84. The impedance matching liquid may be isolated from the patient to avoid direct contact with the liquid. For example, a thin conformal polyethylene liner that can be removed after the exam can be used. While the invention is illustrated herein with regard to breast imaging, it is understood that the present invention may be utilized for imaging other parts of the body of an individual or other objects that include a surface and/or one or more region having different dielectric properties.

In an operation 104, measured electromagnetic field data, denoted ($\bar{E}_m$, $\bar{H}_m$) herein, is formed for each scattered signal received at each of the plurality of antennas. Vector quantities are indicated with boldface type (e.g. v), while electromagnetic fields are denoted by overcasts (e.g. $\bar{E}$). The matrix transpose is denoted by a superscript T (e.g. $M^T$). In an exemplary embodiment, the electromagnetic field data is assumed to follow Maxwell's equations for non-dispersive medium where Ampere's law is given by:

$$\nabla \times \bar{H} = \varepsilon \frac{\partial}{\partial t}\bar{E} + \sigma \bar{E}$$

where $\epsilon(x,y,z)$ is the spatial distribution of the permittivity and $\sigma(x,y,z)$ is the spatial distribution of the conductivity of the target object. In another exemplary embodiment, the electromagnetic field data is assumed to follow Maxwell's equations for dispersive medium where Ampere's law is given by:

$$\nabla \times \bar{H} = \varepsilon_\infty \frac{\partial}{\partial t}\bar{E} + \sigma_s \bar{E} + \bar{J}_d$$

In addition to the losses due to the static conductivity $\sigma_s$, dielectric losses are taken into account through the dispersion current term $\bar{J}_d$. These losses are due to the frequency-dependent dielectric properties. In an exemplary embodiment, the frequency-dependent dielectric properties are assumed to follow the single-pole Debye model:

$$\varepsilon(\omega) = \varepsilon_\infty + \frac{\varepsilon_s - \varepsilon_\infty}{1 + j\omega\tau}$$

where $\epsilon_\infty$ is the permittivity at infinite frequency, $\epsilon_s$ is the static permittivity, $\tau$ is the relaxation time constant, and $\omega$ is the radial frequency. As known to those skilled in the art, other models also capture the frequency dependence of the dielectric properties and may be used without deviating from the scope of the invention.

In an operation 106, the measured field data is saved in a memory for use in signal processing of the measured field data. In an operation 108, a spatial grid of the target object is defined. The spatial grid is a plurality of points regularly spaced throughout the target object in 3-D (x, y, z). A surface location of the target object is determined in an operation 110.

Figure 3:
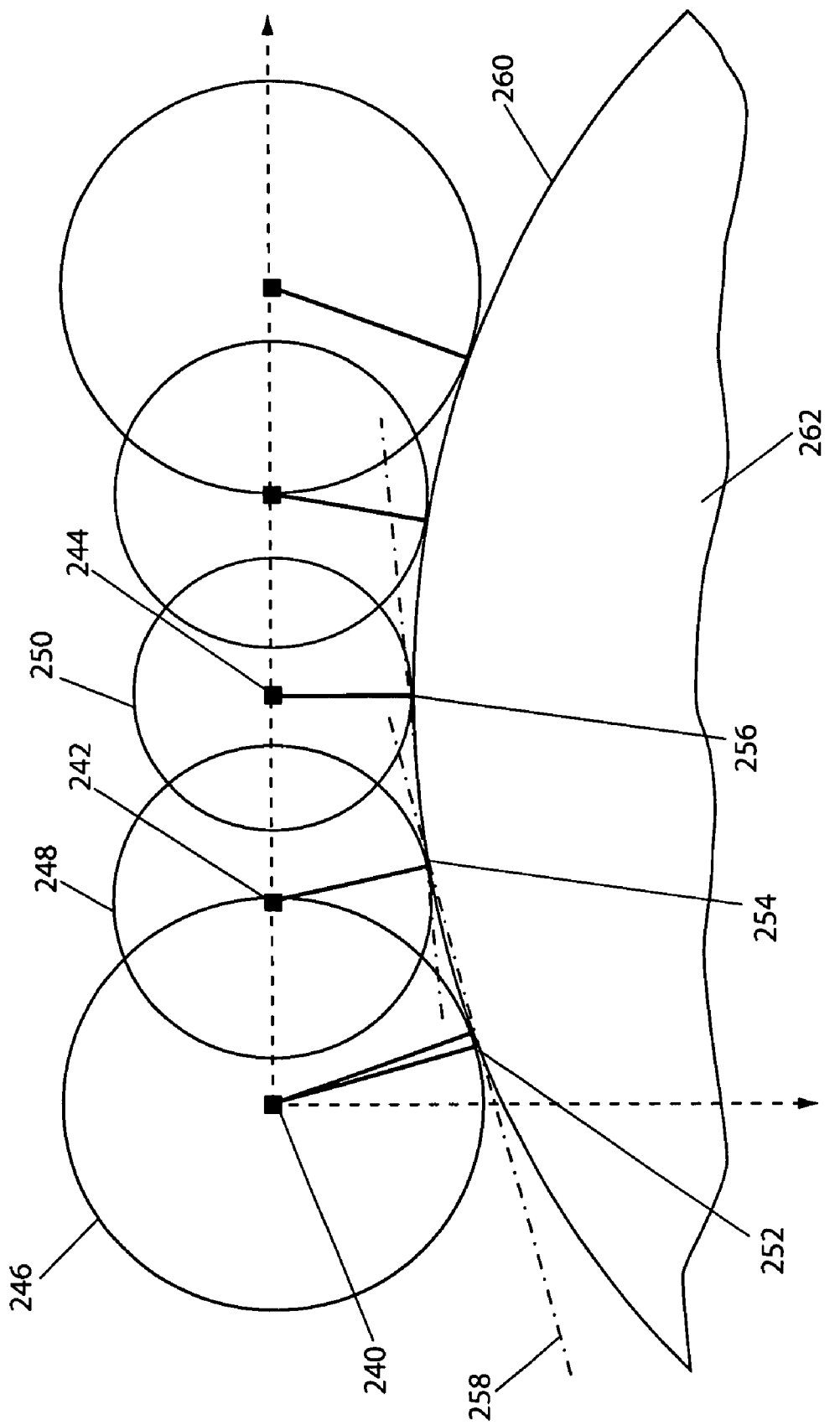
FIG. 3 is an illustration depicting a portion of the breast surface estimation algorithm in accordance with the invention.

An example surface estimation algorithm for a 2-dimensional cross section of a 3-dimensional object is shown with reference to FIG. 3. In the example shown, the surface 260 covers the breast tissue 262. The method is based on geometric principles and the fact that an impedance mismatch at the interface results in significant reflection. A propagation time from the surface to each antenna of the plurality of antennas 240, 242, 244 is estimated. The propagation time locates the surface on a circle 246, 248, 250 centered at the antenna 240, 242, 244 and having a known radius. The surface is assumed to be convex and tangent to the circle. A tangent point 252, 254, 256 defines the intersection of the circle and the breast surface. The tangent point 252, 254, 256 for each antenna 240, 242, 244 is determined by assuming that the circles 246, 248, 250 centered at adjacent antennas are located on the same tangent line 258 defined by the tangent points 252, 254. The surface 260 is estimated to be located at the point where the circle and the shared tangent line between adjacent antennas touch. Multiple tangent points are obtained for each interior antenna. The average of each tangent point may be used as the estimate of the surface location for each interior antenna.

In an operation 112, estimated electromagnetic material parameters are determined. In a non-dispersive medium, the electromagnetic material parameters are $\epsilon$ and $\sigma$. In a dispersive medium described, for example, by a Debye model, the electromagnetic material parameters are $\epsilon_\infty$, $\epsilon_s$, and $\sigma_s$. The estimation of the material parameters uses a time-domain inverse scattering technique as discussed in more detail with reference to FIG. 6.

In an operation 114, the "best estimate" of the electromagnetic material parameters determined in operation 112 is selected from the material parameters defined using the time-domain inverse scattering technique. In an exemplary embodiment, the "best estimate" is selected based on a minimum of a cost function. The cost function represents the difference between the measured field data and the field data calculated using the estimated electromagnetic material parameters. In an operation 116, the target object is imaged using the best estimate of the electromagnetic material parameters for the target object.

The invention can be practiced using various microwave imaging systems based on either microwave tomography or radar principles. In an exemplary embodiment, each antenna in an array of antennas sequentially transmits a low-power, ultra-short microwave pulse or a wideband signal into an object to be imaged, such as the breast, and the remaining antennas of the array of antennas receive the microwave signal reflected from the breast surface and the interior of the breast. The relative arrival times and amplitudes of reflected signals received by the antennas across the antenna array provide information that can be used to detect the presence and determine the location of malignant lesions. The array of antennas may be linear, rectangular, circular, conformal, etc.

Figure 4:
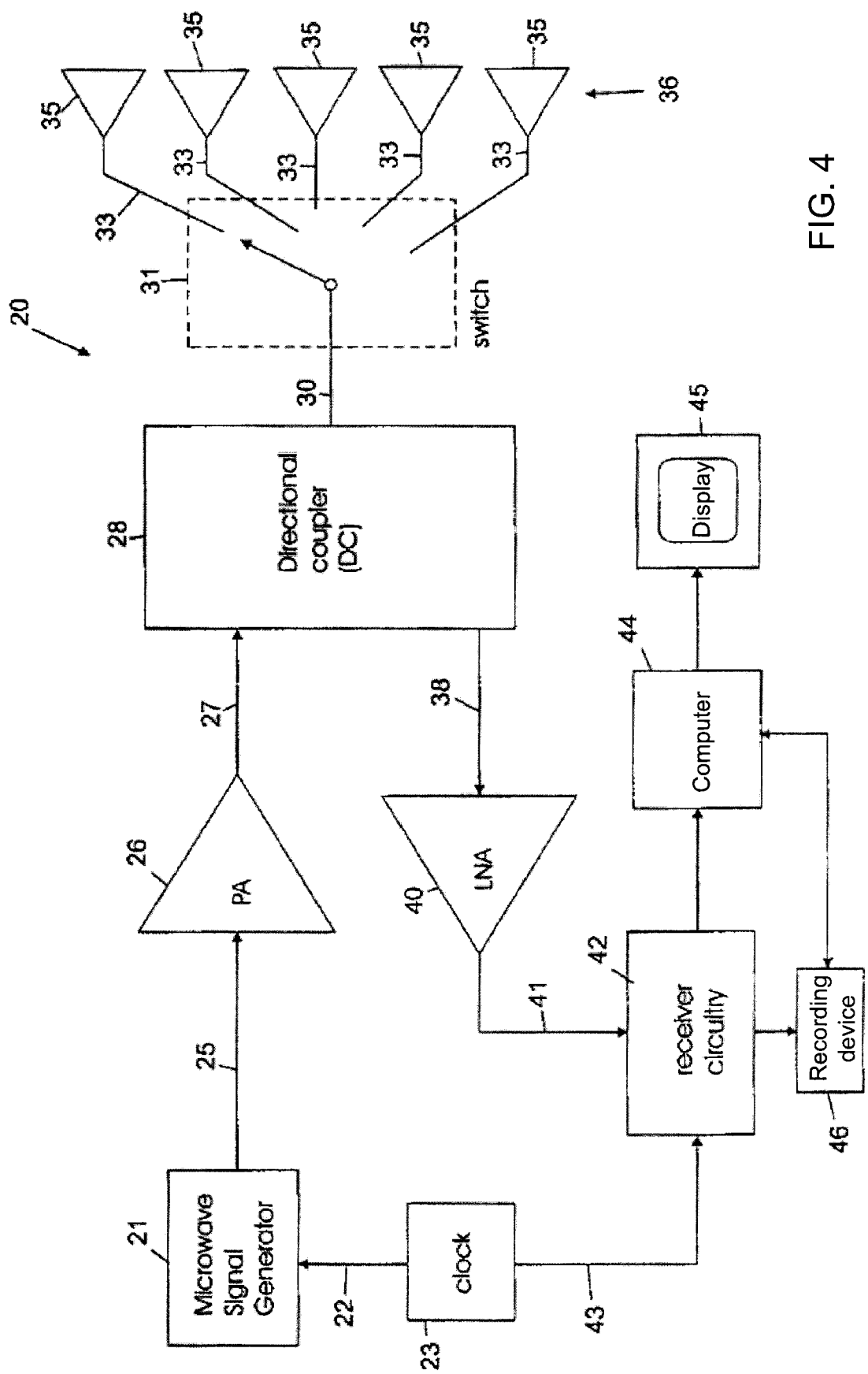
FIG. 4 is a block diagram of a microwave imaging system in accordance with the invention for transmitting and receiving using the same antenna.

With reference to FIG. 4, an exemplary microwave imaging system is shown. Transmission and reception of the microwave signals uses the same antenna and is shown generally at 20. The imaging system 20 includes a microwave signal generator 21 which is supplied, on a line 22, with clock pulses from a clock 23. The output of the signal generator 21 may be short broadband pulses, a signal synthesized from multiple discrete frequencies, a signal synthesized from a frequency swept (chirp) pulse, etc. The output is provided on a line 25 to a power amplifier 26, the output of which is provided on a line 27 to a directional coupler 28. The output of the directional coupler 28 is provided on a line 30 to a switching system 31 which selectively directs the power from the line 30 to lines 33 leading to each of the antennas 35 which are arranged in an array 36 of antennas (e.g., a linear, a rectangular or a circular array).

An array of antennas may be synthesized by using one antenna 35 and moving it from position to position to collect data at each position, although the forming of a "virtual" array in this manner is not preferred. Further, the array may be formed to partially surround the object being imaged, for example, for use in breast imaging the array may be formed to encircle the pendant breast as shown with reference to FIG. 2.

The antennas 35 and other microwave components preferably should be wideband and operate in the 1-10 GHz range. Examples of wideband antenna designs that may be utilized are the "bowtie" and Vivaldi type antennas and horn antennas designed for wideband operation. See X. Li, et al, "Numerical and experimental investigation of an ultrawideband ridged pyramidal-horn antenna with curved launching plane for pulse radiation," IEEE Antennas and Wireless Propagation Letters, vol. 2, pp. 259-262, 2003.

The switch 31 is formed to selectively provide microwave power individually to the antennas 35 from the directional coupler 28 and to receive a signal from that antenna which is directed back through the switch 31 to the directional coupler 28. The directional coupler 28 sends the received signal on a line 38 to a low noise amplifier 40, the output of which is provided on a line 41 to a receiver 42. The receiver 42 also receives clock pulses on a line 43 from the clock 23. The clock pulses on the line 43 allow the receiver 42 to time the onset of pulses of microwave power supplied from the signal generator 21 to allow correlation in time of the received signal with respect to the transmitted signal. Alternatively, the power output from the signal generator 21 may be provided through a power splitter to the receiver 42 to allow time correlation.

The signal generator 21, which may include a computer or digital processor, generates appropriately timed and shaped output pulses, discrete frequencies, chirp pulses, etc., as required for the type of microwave transmission being utilized. The receiver 42 may be of conventional construction, providing detection of the received microwave signal and conversion of the detected signal to digitized data, e.g., with sampling of the received signal after each pulse to build up a digitized waveform, with the digitized data being provided to a digital signal processor of conventional design within the receiver 42 or to an appropriately programmed computer 44 (e.g., a general purpose PC, a dedicated digital signal processor, etc.) all of which will be referred to herein generally as a "processor." It is understood that any type of processor that can be programmed to carry out the signal/data processing set forth herein may be utilized. The digitized data may be saved in a memory coupled to the processor as known to those skilled in the art.

The receiver 42 or the separate computer 44 additionally process the data to provide image data which may be displayed on a display device 45, such as a video display terminal, or which may be transmitted to a recording device 46 such as a magnetic disk or CD ROM for long-term storage, or transmitted for printout, further data processing, etc. A reflection artifact subtraction process (e.g., for the breast surface response or the antenna response) to reduce the effect of the early-time artifact response is performed on the received image data using signal processing techniques. The detection and location of tumors is carried out in a computer in the receiver 42 or a separate computer 44 on the processed data received from the antennas. Signal processing may also be carried out to compensate for frequency dependent scattering. As an example only of commercial instruments that may be utilized, the signal generator 21, amplifiers 26 and 40, directional coupler 28, receiver 42 and clock 23 may be implemented in an Agilent Vector Network Analyzer model 8720 ES, particularly for the discrete frequency based approach, and the computer 44 may be connected to control the signal generator 21 and the switch 31.

Figure 5:
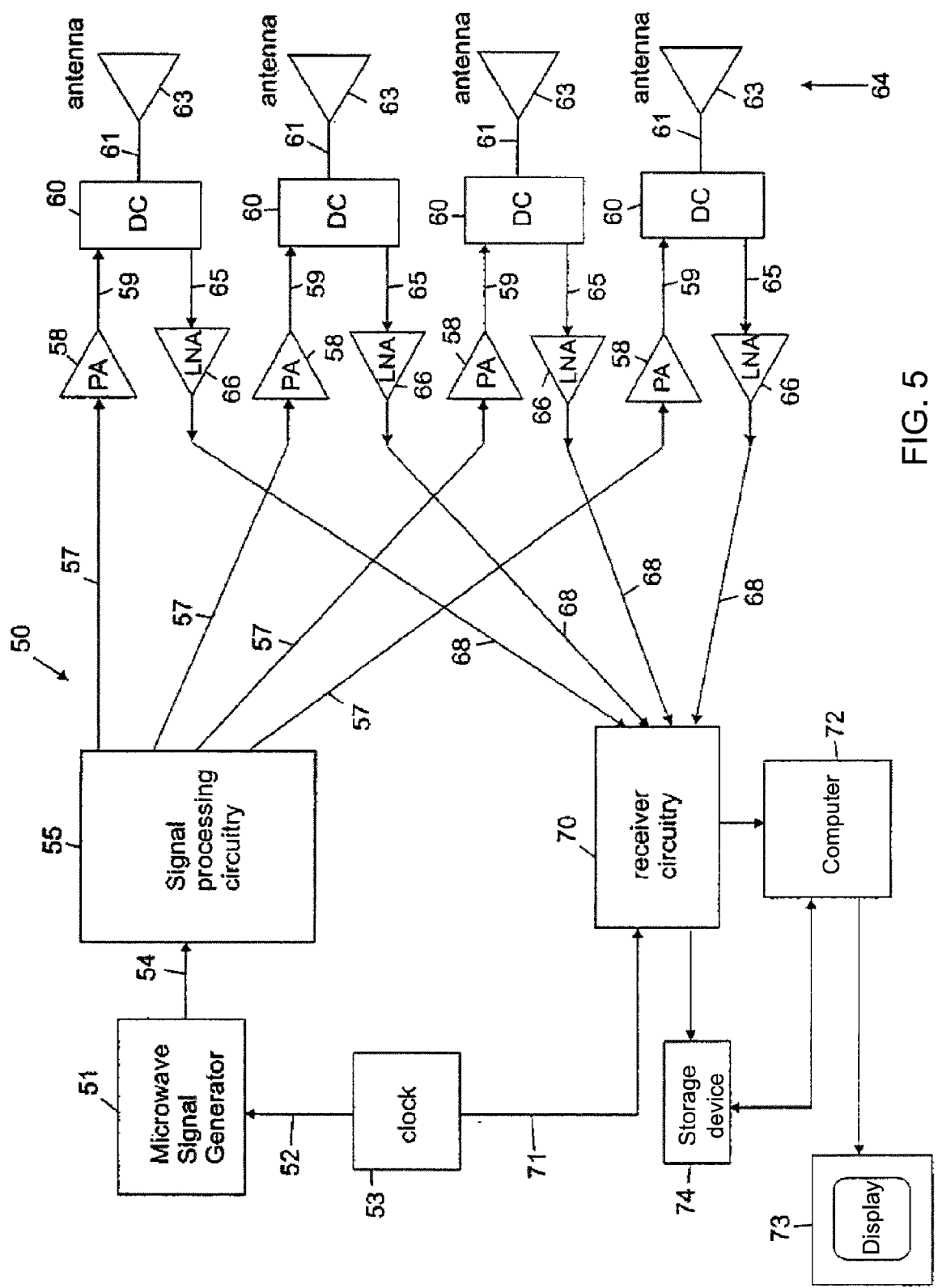
FIG. 5 is a block diagram of a further embodiment of a microwave imaging system in accordance with the invention providing simultaneous transmission and reception with all antennas.

A microwave imaging system which may be utilized for simultaneous transmission from each antenna is shown generally at 50 in FIG. 5. The system 50 includes a signal generator 51 which receives a clock pulse on a line 52 from a clock 53. The output of the signal generator 51 is provided on a line 54 to signal processing circuitry 55 which distributes the microwave (e.g., pulse) output on lines 57 to power amplifiers 58. Each of the power amplifiers 58 provides its output on a line 59 to a directional coupler 60, the output of which is provided on a line 61 to an individual antenna 63. The antennas 63 are arranged to form an array 64 of antennas, e.g., a rectangular array of antennas arranged in rows and columns or a circular array. The array device 80 may be utilized as the antenna array 36 of FIG. 4, with the antenna elements 82 corresponding to the antennas 35, or as the antenna array 64 of FIG. 5, with the antenna elements 82 corresponding to the antennas 63.

The signal processing circuitry 55 distributes a microwave pulse on each of its output lines 57 with frequency dependent filtering to provide the desired microwave radiation from the antenna array 64, e.g., focusing of radiated power from the array 64 to selected points in the target object. The signals picked up by each antenna 63 are transmitted back on the line 61 to the directional coupler 60. The directional couplers provide the received signals on lines 65 to low noise amplifiers 66, the outputs of which are provided on lines 68 to a receiver 70. The receiver 70 also receives the clock pulses from the clock 53 on a line 71 to allow the receiver 70 to time the received signals with respect to the transmitted signals.

The receiver 70 detects the microwave signal on a line 68 and converts the received signal to digital waveform data which is processed by a digital signal processor or a computer 72 in accordance with the invention. The image data from the computer 72 or digital signal processor may be displayed, e.g., on a video display terminal 73, or provided to a storage device 74, e.g., CD ROM, magnetic disk, tape, etc. for long-term storage, or transmitted for other purposes. Breast surface location, reflection artifact removal (such as breast surface response removal), electromagnetic parameter estimation, beam forming, tumor detection through hypothesis testing, frequency-dependent scattering processes, etc., may be carried out in a separate computer (e.g., the computer 44 of FIG. 2 or 72 of FIG. 3), or in a digital signal processor of the receiver (e.g., the receiver 42 of FIG. 2 or the receiver 70 of FIG. 3), both of which will be referred to herein as a processor, that is programmed to carry out the processing on the measured field for each antenna that is provided by the receiver.

To achieve the best resolution of the reconstructed image, the radiated microwave pulse is preferably relatively short (e.g., about 100 ps), has a wide band of frequency content, typically from 0 to 20 GHz, with significant energy in the frequency range of 1 GHz to 10 GHz. It is desirable to utilize antennas that are suitable for transmitting and receiving such short pulses with minimum distortion or elongation. It is further desirable that the pulse radiating antenna have a constant sensitivity and a linear phase delay over the bandwidth of the incident electromagnetic pulse in the frequency domain. It is also desirable that the antenna design suppress both feed reflection and antenna ringing, and that the antenna have a smooth transition from the cable impedance at the feed point to the impedance of the immersion medium at the radiating end of the antenna. The return loss, S11, should be low in magnitude as less return loss means more power is transmitted to the antenna. Ideally, the return loss should be constant over the required bandwidth so that the spectrum of the transmitted power is flat and should have a linear phase delay across the frequency band so that the radiated waveform will not be dispersed. Other desirable properties include a well-defined polarization, constant gain, and low side lobes in the radiation pattern. Resistively loaded cylindrical and conical dipole (monopole), and bow-tie antennas can be utilized for radiating temporally short, broad bandwidth pulses. Resistive loading can be utilized to reduce the unwanted reflections that occur along the antenna and the associated distortion of the radiated signal. Spiral antennas and log-periodic antennas have also been designed to achieve wide bandwidth. Spectrum shaping and RF filtering may be needed to enhance the frequency performance of these antennas. Specialized antennas designed for pulse radiation may also be utilized. An example of a suitable antenna that is designed for short pulse radiation is shown and described in U.S. Pat. No. 6,348,898, issued Feb. 19, 2002.

The methods described above assume only one antenna is transmitting and receiving at any point in time. This process involves sequentially stepping through the array. If an antenna array with multiple receive channels is used as shown in FIG. 5, then a multitude of different transmit-receive strategies are possible. Tumor detection/location and breast surface response removal algorithms may be utilized in which all antennas receive simultaneously. Transmit strategies may also be utilized that focus the transmitted energy on a given region of the breast. The transmit and receive focus location is then scanned throughout the breast to form the image of scattered power. Such scanning may be utilized to improve resolution and robustness to artifacts, noise, and clutter. The signal parameters used to focus the transmission are the relative transmit time and signal amplitude in each antenna. After a lesion is located, the transmitted energy from the antennas may be focused on the lesion at a higher power level to heat and destroy the lesion.

An exemplary sensor in the imaging system may include a microwave vector reflectometer (the pulse generator 21, 51 and receiver 42, 70, and may include the associated amplifiers and directional couplers) and a low-reverberation ultrawideband transmitting/receiving antenna. A low-noise commercial vector network analyzer (VNA) with a time-domain option may be used for the vector reflectometer. The dynamic range of a VNA of this type is sufficient to detect small malignant tumors up to depths of 5.0 cm in the breast.

Figure 6:
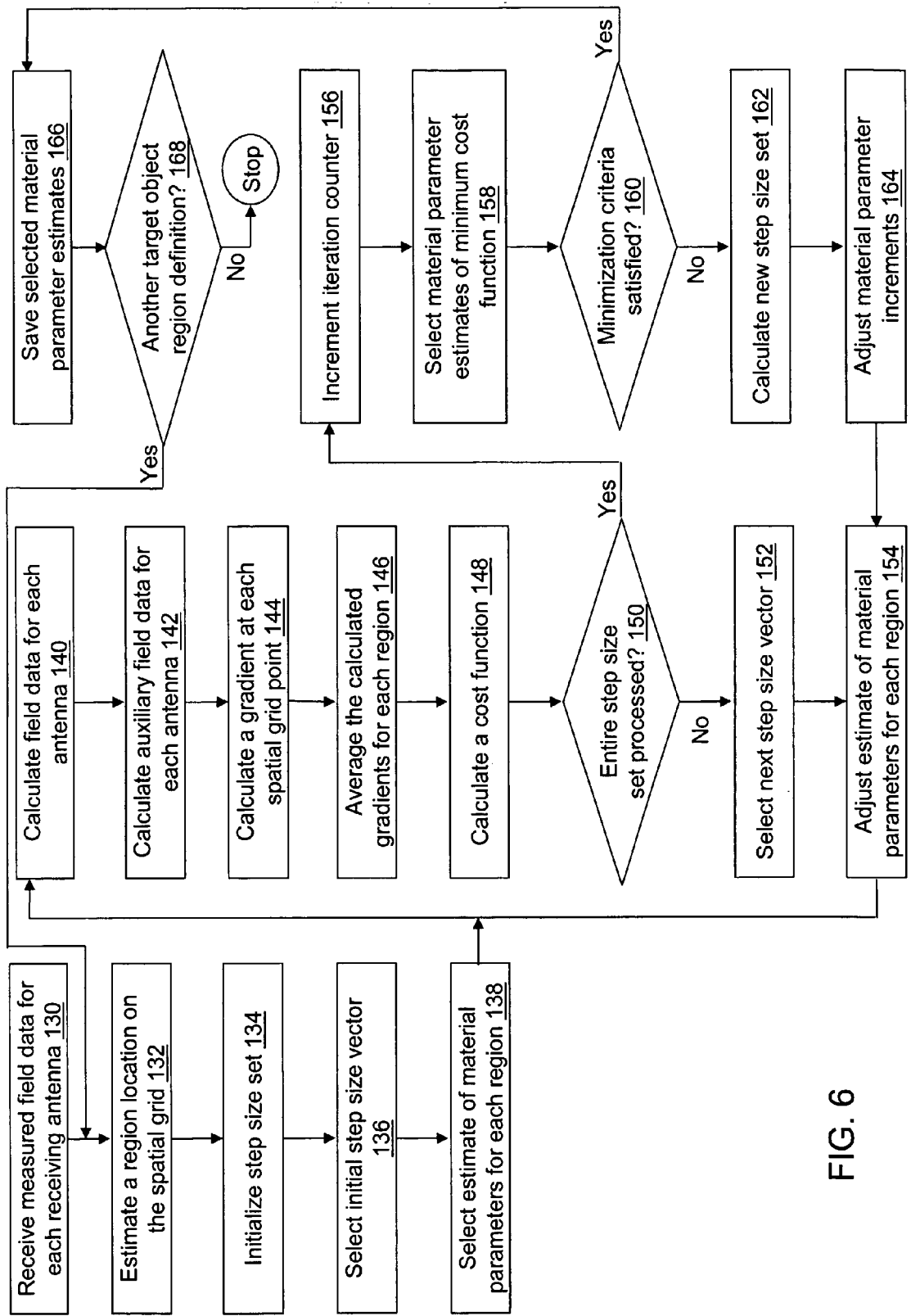
FIG. 6 is a flow diagram illustrating exemplary operations of an electromagnetic material parameter estimation system in accordance with the invention.

With reference to FIG. 6, exemplary operations of the time-domain inverse scattering technique for estimating the electromagnetic material parameters are shown. In an operation 130, the measured field data for each receiving antenna is received as an input to the time-domain inverse scattering technique. For example, the measured field data may be accessed from a memory by a processor. In an operation 132, one or more regions within the target object are defined and the location of each region is estimated on the spatial grid. The estimated region locations are called the reconstruction model because they dictate the geometry of the final solution.

Figure 7:
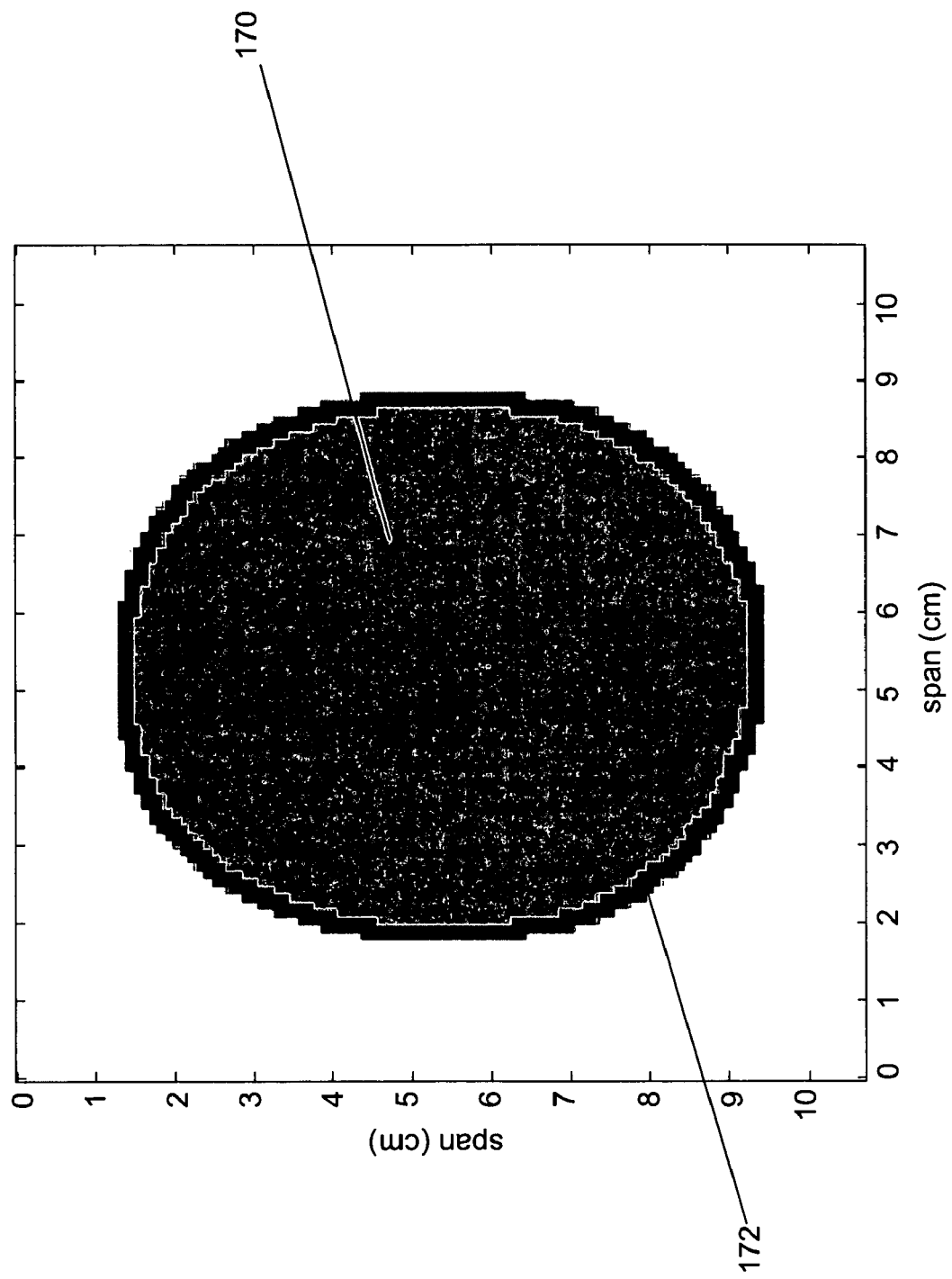
FIG. 7 depicts a 2-D reconstruction model of the breast including the skin region and the breast tissue region.

For example, in breast imaging, the skin thickness is not known a priori and is expected to vary from patient to patient. Additionally, the electromagnetic properties of skin varies from that of breast tissue. Thus, the skin tissue layer and the breast tissue define two different regions for estimating electromagnetic properties as shown with reference to FIG. 7. The first region 170 includes the breast tissue and the second region 172 includes the skin layer that assumes a skin thickness of 2 mm in this example. The surface of the target object was determined for the skin surface as described with reference to FIG. 3 and the assumed skin thickness was added to form the second region 172. The remaining interior defines the breast tissue region. A set of skin thicknesses may be used to improve the determination of the electromagnetic material parameters of the breast tissue and the surrounding skin layer. The normal range of skin thickness across the breast is 0.5-2.7 mm. Thus, in an exemplary embodiment, the skin thickness may be selected from a set of skin thicknesses such as {1.0, 2.0, 3.0} mm. The first region 170 and the second region 172 are defined for each skin thickness resulting in a different estimation of the average electromagnetic parameters for each region.

Before proceeding with a description of FIG. 6, a mathematical description of the time-domain inverse scattering technique is described. Relative to the time-domain inverse scattering technique, a cost function F is formed, which measures the squared difference between the measured fields ($\overline{E}_m$, $\overline{H}_m$) and the numerically calculated fields ($\overline{E}_c$, $\overline{H}_c$) at each of K antennas over a time interval [0,T]:

$$F = \sum_{a=1}^{K} \sum_{b=1}^{K} \int_0^T \left[ \left\| \begin{pmatrix} \overline{E}_m^a(x,y,z,t) - \\ \overline{E}_c^a(x,y,z,t) \end{pmatrix} \delta(x-x_b, y-y_b, z-z_b) \right\|^2 + \eta^2 \left\| \begin{pmatrix} \overline{H}_m^a(x,y,z,t) - \\ \overline{H}_c^a(x,y,z,t) \end{pmatrix} \delta(x-x_b, y-y_b, z-z_b) \right\|^2 \right] dt$$

where superscript a denotes the transmitting antenna, ($x_b, y_b, z_b$) are the coordinates of the $b^{th}$ receiving antenna, $\delta$ is the Dirac delta-function, and $\eta$ is the intrinsic impedance of the known immersion medium. The calculated fields ($\overline{E}_c$, $\overline{H}_c$) are obtained from a finite-difference time-domain (FDTD) simulation of the target object V which uses the current estimated dielectric property distributions. The objective is to minimize the cost F as a function of the estimated distributions. This may be accomplished using a steepest-descent method, which requires knowledge of the derivatives of the cost function with respect to the unknown properties at the discrete locations in V.

To define the partial derivatives of the cost function with respect to the electromagnetic material parameters at a point in space, a set of auxiliary field variables denoted by $\overline{e}(x,y,z,t)$ and $\overline{h}(x,y,z,t)$ are introduced. See Rekanos, "Time-domain inverse scattering using Lagrange multipliers: An iterative FDTD-based optimization technique," Journal of Electromagnetic Waves and Applications, Vol. 17, pp. 271-289 (2003) and Takenaka, et al, "Inverse scattering for a three-dimensional object in the time domain," Journal of the Optical Society of America: A, Vol. 20, No. 10, pp. 1867-1874 (2003) for additional detail. These new variables satisfy a set of equations similar to Maxwell's equations and have their own initial conditions. Assuming antenna a is transmitting, the auxiliary field variables satisfy:

$$\nabla \times \overline{h}^a + \left(\varepsilon \frac{\partial}{\partial t} - \sigma\right) \overline{e}^a = \sum_{\substack{b=1 \\ b \neq a}}^{K} (\overline{E}_m^a - \overline{E}_c^a) \delta(x-x_b, y-y_b, z-z_b) \quad (1)$$

$$\nabla \times \overline{e}^a - \mu \frac{\partial}{\partial t} \overline{h}^a = \eta^2 \sum_{\substack{b=1 \\ b \neq a}}^{K} (\overline{H}_m^a - \overline{H}_c^a) \delta(x-x_b, y-y_b, z-z_b) \quad (2)$$

where $\overline{e}|_{t=T} = \overline{h}|_{t=T} = 0$. By comparing (1) and (2) to Maxwell's equations, it can be shown that a change of variable allows the calculation of the auxiliary fields via a standard FDTD simulation. Because the calculated fields ($\overline{E}_c, \overline{H}_c$) appear in (1) and (2), an initial FDTD simulation must be performed to generate these field quantities. A second FDTD simulation can be carried out to generate the auxiliary fields $\overline{e}(x,y,z,t)$ and $\overline{h}(x,y,z,t)$. Specifically, after incorporating the estimated dielectric distributions into the FDTD grid, adjoint fields may be obtained by 1) time-reversing the error signals being used for source terms, 2) multiplying the electric error signals by −1, 3) running the FDTD simulation, and 4) time-reversing the resulting adjoint fields saved within V.

This two-step procedure is repeated for each remaining antenna in the array. As a result, 2K simulations are required for every iteration of the inverse scattering algorithm. The stored field values are used to calculate the gradients of the cost function F with respect to the permittivity and conductivity at $(x_o; y_o; z_o)$:

$$\frac{\partial F}{\partial \varepsilon(x_o, y_o, z_o)} = -\sum_{a=1}^{K} \int_0^T \overline{e}^a(x_o, y_o, z_0, t) \cdot \frac{\partial E_c^a(x_o, y_o, z_0, t)}{\partial t} dt \quad (3)$$

$$\frac{\partial F}{\partial \sigma(x_o, y_o, z_o)} = -\sum_{a=1}^{K} \int_0^T \overline{e}^a(x_o, y_o, z_0, t) \cdot \overline{E}_c^a(x_o, y_o, z_o, t) dt \quad (4)$$

The unknown medium properties are contained in the vector $p=[\epsilon(1_1)\sigma(1_1)\ldots\epsilon(1_p)\sigma(1_p)]^T$ where $1_i$ represents $(x_i; y_i; z_i)$ and P is the number of positions within V at which the dielectric properties are to be estimated. The gradient of F with respect to the dielectric properties is denoted by $$g = \frac{\partial F}{\partial p}.$$

A conjugate-gradient method iteratively updates the 2P unknowns using the gradient g:

$$p_{n+1} = p_n + \alpha_n d_n \quad (5)$$

$$d_n = \begin{cases} -g_n & \text{if } n = 1, \\ \beta_n d_{n-1} - g_n & \text{if } n > 1, \end{cases} \quad (6)$$

where $\alpha_n$ is the step-size parameter for the $n^{th}$ iteration and $\beta_n$ is the memory parameter for the $n^{th}$ iteration. See Y. H Dai, "A family of hybrid conjugate gradient methods for unconstrained optimization," Mathematics of Computation, Vol. 17, No. 2, pp. 1317-1328 (2003) for additional detail. The storage required to calculate all of the gradients is 4KPS, where S is the number of time steps in each FDTD simulation. The dependence of the storage upon P is a strong motivation to use as course a reconstruction mesh as possible.

The previous derivation assumed that the electromagnetic waves propagating within V obey Maxwell's equations for non-dispersive medium. For a Debye dispersive medium, if $\tau$ is assumed known, then the number of unknown material parameters per region increases from two $(\epsilon,\sigma)$ to three $(\epsilon_\infty, \epsilon_s, \sigma_s)$. This assumption is not unreasonable because the time constants of the first poles of the Cole-Cole models for fat, muscle, and skin are all very similar. With this assumption and under the condition that the maximum frequency of the source $\omega_{max}$ is low enough such that $(\omega_{max}\tau)^2 \ll 1$, formulas for the derivatives of the cost function with respect to the dispersive material parameters may be derived as:

$$\frac{\partial F}{\partial \varepsilon_\infty(x_o, y_o, z_o)} = -\sum_{a=1}^{K} \int_{t=0}^{T} \overline{e}^a(x_o, y_o, z_o) \cdot \frac{\partial \overline{E}^a(x_o, y_o, z_o, t)}{\partial t} dt \quad (7)$$

$$\frac{\partial F}{\partial \sigma_s(x_o, y_o, z_o)} = -\sum_{a=1}^{K} \int_{t=0}^{T} \overline{e}^a(x_o, y_o, z_o, t) \cdot \overline{E}^a(x_o, y_o, z_o, t) dt \quad (8)$$

$$\frac{\partial F}{\partial \varepsilon_\Delta(x_o, y_o, z_o)} = -\sum_{a=1}^{K} \int_{t=0}^{T} \overline{e}^a(x_o, y_o, z_o, t) \cdot \overline{J}_d^a(x_o, y_o, z_o, t) dt \quad (9)$$

where $\epsilon_\Delta = \epsilon_s - \epsilon_\infty$. As related previously, the adjoint fields may be determined by 1) time-reversing the error signals being used for source terms, 2) multiplying the electric error signals by −1, 3) running the FDTD simulation, and 4) time-reversing the resulting adjoint fields saved within V.

To apply the time domain inverse scattering technique, two things must be known: 1) closed-form equations for the derivative of the cost function with respect to the dispersive material parameters ($\epsilon_\infty$, $\epsilon_s$, $\sigma_s$), and 2) equations governing the behavior of the adjoint fields. With one exception, the steps in the derivations of the non-dispersive, voxel-based algorithm can be modified in a straightforward manner to obtain a dispersive algorithm. Integration-by-parts is used to switch the partial derivative operation from the calculated field data to adjoint fields within a time integral. Alternatively, the product rule is used to switch a temporal partial derivative from the calculated field data to adjoint fields. Both approaches can be seen as equivalent, with the result being the same:

$$\int_{t=0}^{T} \overline{e} \cdot \varepsilon \frac{\partial}{\partial t} \delta \overline{E} dt = \varepsilon[\overline{e} \cdot \delta \overline{E}]_{t=0}^{t=T} - \varepsilon \int_{t=0}^{T} \delta \overline{E} \cdot \frac{\partial}{\partial t} \overline{e} dt \quad (10)$$

$$= -\varepsilon \int_{T=0}^{T} \delta \overline{E} \cdot \frac{\partial}{\partial t} \overline{e} dt$$

Equation (10) allows the formulas governing the behavior of the adjoint equations to be determined, which in turn allows for the derivation of the gradient formulas. This derivation is repeated for the dispersion current term. In the frequency domain:

$$\overline{J}_d(\omega) = \varepsilon_\Delta \frac{j\omega}{1 + j\omega\tau} \overline{E}(\omega), \quad (11)$$

where $\overline{J}_d(\omega)$ and $\overline{E}(\omega)$ are the Fourier transforms of $\overline{J}_d$ and $\overline{E}$ respectively, and $j=\sqrt{-1}$. If $(\omega_{max}\tau)^2 \ll 1$, then:

$$\overline{J}_d(\omega) \approx \epsilon_\Delta j\omega(1 - j\omega\tau)\overline{E}(\omega) \quad (12)$$

Transforming back into the time-domain shows that the dispersion current is approximately a scaled combination of the first and second derivatives of the electric field. By performing integration-by-parts (or the product rule) twice, it can be shown that the dispersive adjoint fields follow a time-reverse version of Maxwell's equations for dispersive materials.

The time domain inverse scattering technique discretizes the space V into a grid and estimates the dielectric properties at each grid point. V, however, may be defined as the union of $L \geq 1$ disjoint homogeneous regions (e.g. skin layer and breast tissue regions). Given the approximate locations of each of the L regions, a transmitted signal f(t), and a set of measured signals ($\bar{E}_m$, $\bar{H}_m$), the average material parameters can be estimated for each of the regions to approximately produce the measured fields when probed with the transmitted signal. V may be defined to contain two distinct regions, the skin layer and the breast tissue region. Given two regions, there are four unknowns for a non-dispersive medium $\hat{p}=[\epsilon_1 \sigma_1 \epsilon_2 \sigma_2]^T$ and six unknowns for a dispersive medium $\hat{p}=[\epsilon_{\infty 1} \sigma_{s1} \epsilon_{s1} \epsilon_{\infty 2} \sigma_{s2} \epsilon_{s2}]^T$.

The calculation of the gradient of F with respect to $\hat{p}$ first involves the calculation of the gradients at each sampled point in V according to (7) and (8). The grid gradients corresponding to locations in the first region are averaged, and the grid gradients corresponding to locations in the second region are averaged resulting in a gradient for each of the unknown material parameters of $\hat{p}$. By averaging the gradients within each region, the solution is constrained to a specific geometry. This constraint aids in making the problem more well-posed and can lead to increased accuracy. Results also indicate that gradient averaging may also provide robustness with respect to noisy data.

The cost function F is minimized using a conjugate-gradient method where each of the unknown material parameters in $\hat{p}$ is assigned its own step size to form a step size vector. Additionally, each step size is allowed to adapt as a function of the iteration number. As a result, the rate of convergence and the likelihood of converging to the global minimum is increased. The step size vector is defined at iteration n for a non-dispersive medium as $\alpha(n)=[\alpha_{\epsilon 1}(n)\alpha_{\sigma 1}(n)\alpha_{\epsilon 2}(n)\alpha_{\sigma 2}(n)]^T$ where the set of unknowns is defined as $A=\{\epsilon_1, \sigma_1, \epsilon_2, \sigma_2\}$ and for a Debye dispersive medium as $\alpha(n)=[\alpha_{\epsilon \infty 1}(n)\alpha_{\sigma s1}(n)\alpha_{\epsilon s1}(n)\alpha_{\epsilon \infty 2}(n)\alpha_{\sigma s2}(n)\alpha_{\epsilon s2}(n)]^T$ where the set of unknowns is defined as $A=\{\epsilon_{\infty 1}, \sigma_{s1}, \epsilon_{s1}, \epsilon_{\infty 2}, \sigma_{s2}, \epsilon_{s2}\}^T$. Each parameter $\alpha_i(n)$, $i \in A$, is chosen to be either zero or a step size adjustment parameter $R_i(n)$, where $R_i(n)>0$. Given four elements in A and two possible values for each $\alpha_i(n)$, there are 16 possible combinations for the vector $\alpha$. The 16 combinations form a step size set. Given six elements in A and two possible values for each $\alpha_i(n)$, there are 64 possible combinations for the vector $\alpha$. The 16/64 combinations form a step size set. A direct search for the "best estimate" is performed by evaluating the cost function F under each of the 16/64 cases to determine the step size vector that evaluates to the smallest value for F.

The value of the step size adjustment parameter $R_i(n)$ is chosen using:

$$R_i(n) = \begin{cases} 0.85 R_i(n-1) & \text{if } \alpha_i(n-1) = 0 \\ 1.15 R_i(n-1) & \text{if } \alpha_i(n-1) > 0 \end{cases} \quad (13)$$

where $i \in A$. The purpose of (13) is to increase the step size at the next iteration when the current step size is non-zero, thereby increasing the speed of convergence, and to decrease the step size at the next iteration when the current step size is zero, thereby forcing the algorithm to verify that the global minimum is not passed over during the next iteration. Investigation indicates that the step size adjustment parameter $R_i(n)$ can be initialized to a wide range of values with the technique still converging to the same solution.

With reference to FIG. 6, in an operation 134, the step size set is initialized based on $\hat{p}$ as, for example, 16 or 64 step size vectors. The initial step size vector is selected from the step size set in an operation 136. Initial estimates for the parameters of $\hat{p}$ are selected in an operation 138. In an operation 140, the field data for each antenna is calculated to form ($\bar{E}_c$, $\bar{H}_c$). In an operation 142, the auxiliary field data for each antenna is calculated to form $\bar{e}(x,y,z,t)$ and $\bar{h}(x,y,z,t)$. In an operation 144, the gradient g for each parameter of $\hat{p}$ at each spatial grid point is calculated. In an operation 146, the gradient g at each grid point corresponding to locations in the first region are averaged, and the gradient g at each grid point corresponding to locations in the second region are averaged resulting in a gradient for each parameter of $\hat{p}$. Additional regions may be defined. The cost function F is calculated in an operation 148.

The test at operation 150 determines if processing of an additional step size vector is to be performed. If the entire step size set has not been processed, processing continues at operation 152 with the next step size vector. Otherwise, processing continues at operation 156. At operation 152, the next step size vector is selected from the step size set. In an operation 154, the material parameters of $\hat{p}$ are adjusted based on the step size vector and gradient $g_n$ in accordance with equations (5) and (6) where $g_n$ is the same for each step size vector of the step size set. Processing with the adjusted material parameters continues at operation 140.

In an operation 156, an iteration counter n is incremented. The material parameters calculated for each step size vector of the step size set are compared to select the $\hat{p}$ providing the minimum value for the cost function F. This set of material parameters $\hat{p}$ provides the current "best estimate" of the material parameters. The test at operation 160 determines if the minimization criteria for the time-domain inverse scattering technique is satisfied. Example minimization criteria may be the number of iterations n exceeding a stop iteration number, the cost function F falling below a minimum cost function threshold, a change in the cost function F that fall below a change threshold, a change in the estimated parameters $\hat{p}$ as compared to the previous step that falls below an adjustment threshold, etc.

If the minimization criteria is not satisfied, in an operation 162, a new step size set $\alpha_n$ is calculated using the gradients associated with the minimum cost function determined in operation 158. The material parameter increments $d_n$ for each parameter of $\hat{p}$ are calculated in an operation 164. The adjusted material parameter increments $d_n$ for each parameter are used in operation 154 to adjust the material parameters $\hat{p}$ for the next iteration. If the minimization criteria is satisfied, in an operation 166, the selected material parameter estimates are saved for possible use in imaging the target object. The test at operation 168 determines if another target object region definition is to be processed. For example, a new skin thickness may be selected and used to define new estimated region locations for the breast. If there is another region definition to process, processing continues in operation 132 with the new region definition. If there is not another region definition to process, the electromagnetic material parameter estimation process is complete. The "best estimate" of the electromagnetic material parameters can be selected from the saved material parameter estimates of operation 166.

Figure 8:
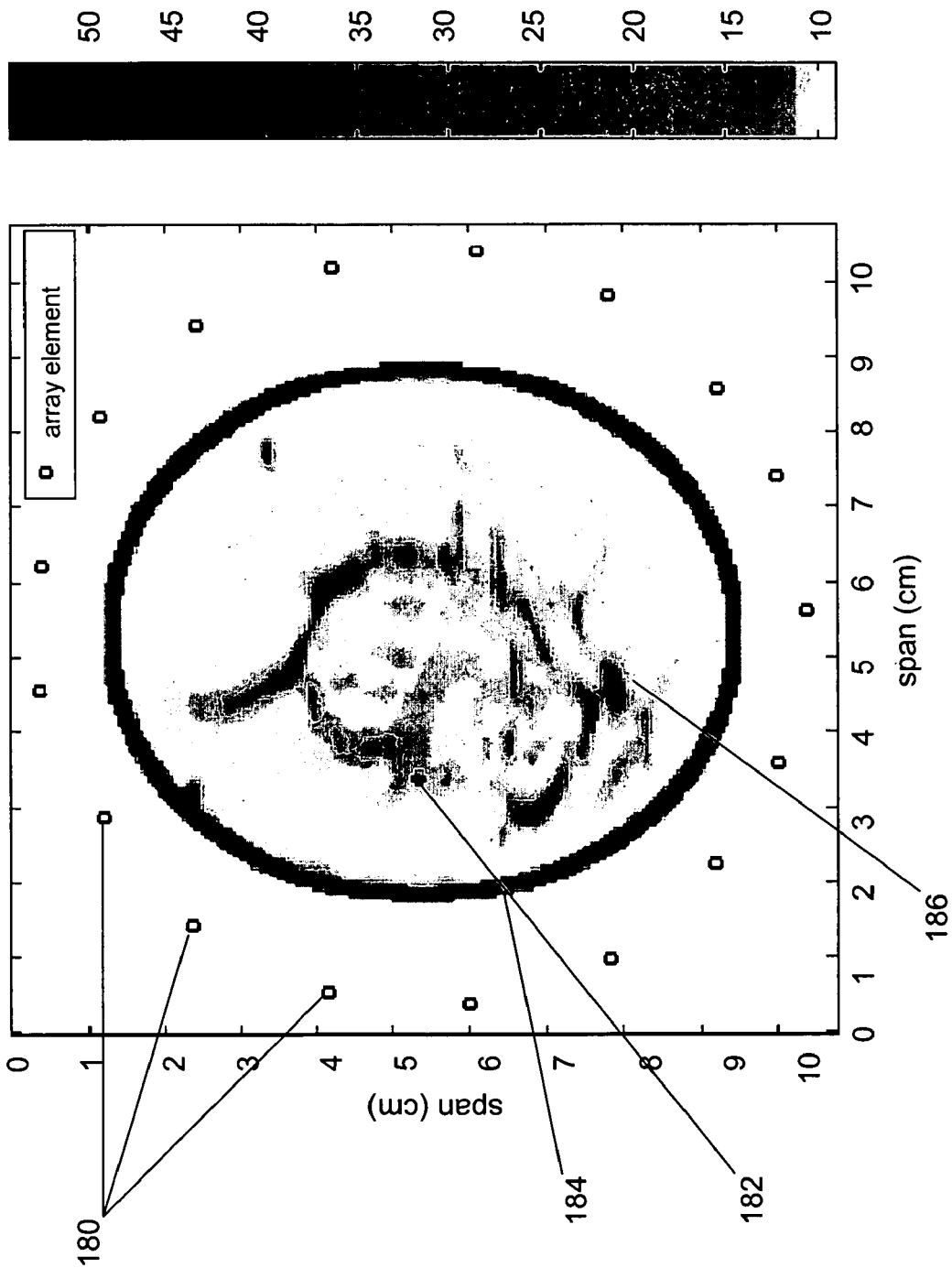
FIG. 8 is an illustrative view of an antenna array in the microwave imaging system of the invention and a 2-D magnetic resonance image (MRI) of a breast including a breast tumor.

With reference to FIG. 8, a 2-D magnetic resonance image (MRI) of a breast including a breast tumor 182 is shown. The breast is shown surrounded by antennas 180 arranged to surround the breast as shown with reference to FIG. 2. The skin layer 184 surrounds the breast tissue 186. In the system configuration shown, the patient lays in the prone position with the breast encircled by a 10-cm-diameter 17-element antenna array. The breast and array are immersed in an oil bolus ($\epsilon_r$=2.6, $\sigma$=0.05 S/m) serving as a coupling medium. The grayscale display of the interior of the breast shows the anatomically realistic variations of the dielectric constant derived from a high-resolution MRI data set.

To demonstrate the effectiveness of the time domain inverse scattering technique a numerical breast model was created for use in FDTD simulations of the data acquisition process. The conversion of MRI pixel intensity to breast tissue permittivity and conductivity employed a piecewise linear mapping that assumed that fatty and fibroglandular tissue have distinct dielectric properties. This conversion process segmented the histogram of MRI pixel intensity into three regions: fatty, fibroglandular, and transition. Visual examination of the MRI was used to determine intensity thresholds for identifying the three regions. The peak in the histogram for the fatty region was set to ($\epsilon_r$=11.4, $\sigma$=0.0962 S/m). The maximum (minimum) fatty tissue pixel intensity was set to 0:9 times (1:1 times) the peak fatty dielectric properties, with the pixel intensities in between being linearly mapped to the ranges between the two extremes and the peak. The same procedure was repeated for the fibroglandular tissue region. The pixel intensities in the transition region were linearly mapped from the upper limit of the fat range to the lower limit of the fibroglandular range to preserve the distinction between fatty and fibroglandular tissue. A 2-mm-diameter malignant tumor with the properties of muscle ($\epsilon_r$=55.6 and $\sigma$=0.879 S/m) was inserted into the breast model at location (3:4 cm, 5:4 cm). A layer of dry skin ($\epsilon_r$=42.7 and $\sigma$=0.80 S/m) with a thickness of 2 mm was added to the model.

Figure 9:
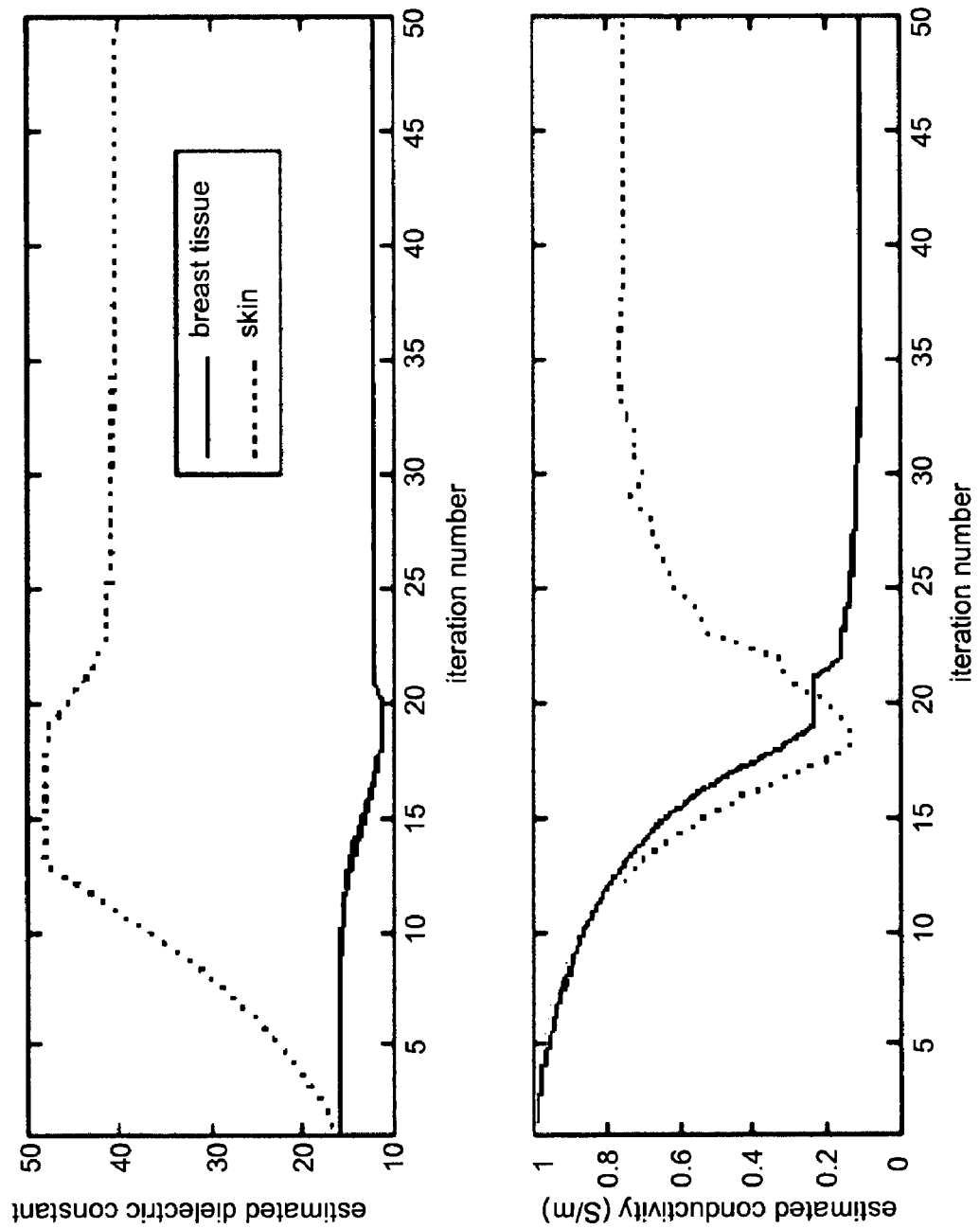
FIG. 9 depicts a progression of the average dielectric properties estimated using the time domain inverse scattering technique in accordance with the invention for the case of a known skin thickness.
Figure 10:
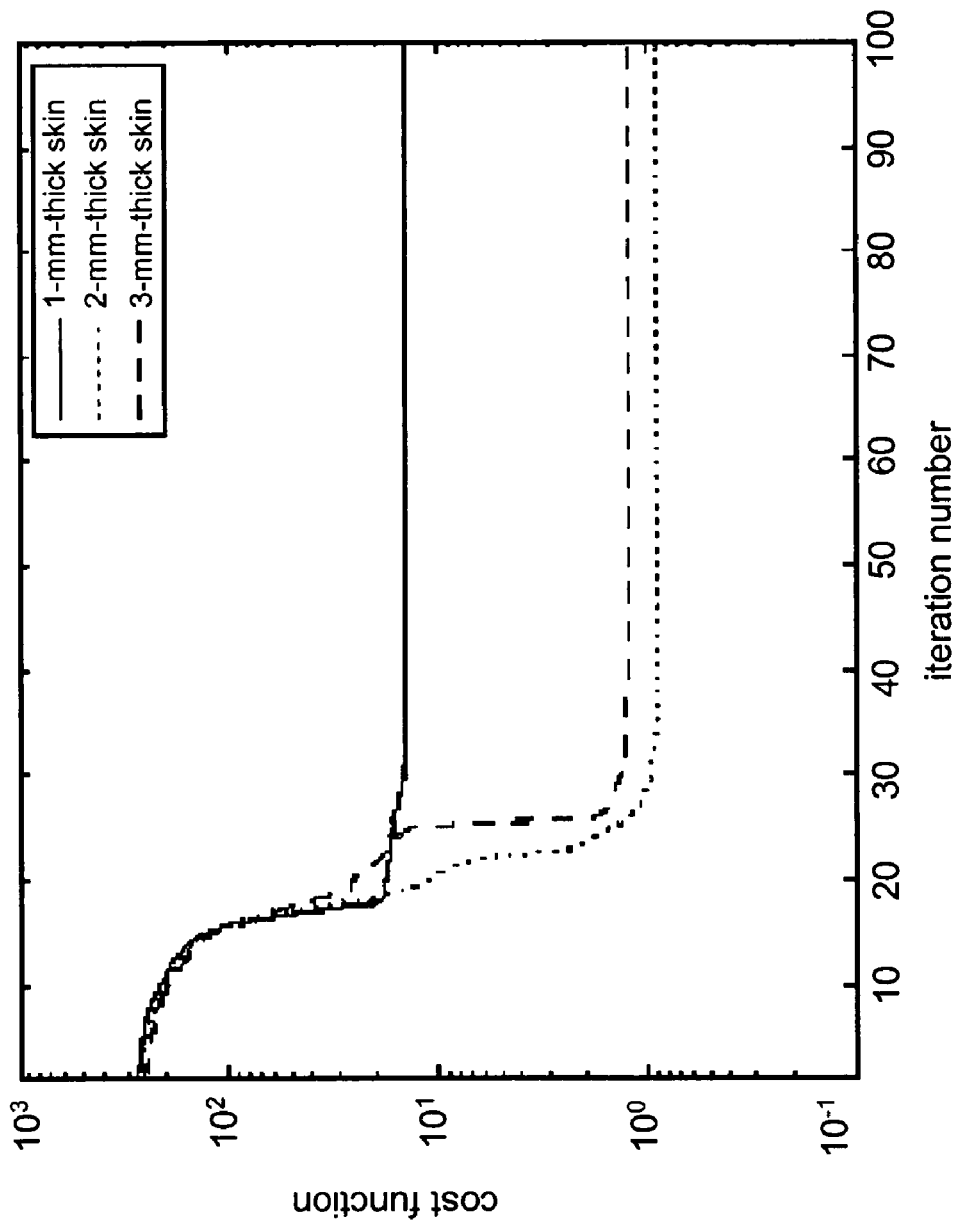
FIG. 10 depicts the cost function as a function of the iteration number for different assumed skin thicknesses wherein the cost function is calculated using the time domain inverse scattering technique in accordance with the invention assuming a non-dispersive medium.

FIG. 9 shows the progression of the time domain inverse scattering technique over the course of 50 iterations for the case of the breast model and assuming a non-dispersive medium. FIG. 10 shows the cost function progression for three different assumed skin thicknesses, 1 mm, 2 mm, and 3 mm, assuming the non-dispersive medium. The average skin thickness that best fits the actual skin layer corresponds to the lowest value of the cost function. The correct 2 mm assumption for the skin layer clearly obtained the best fit to the data.

Figure 12:
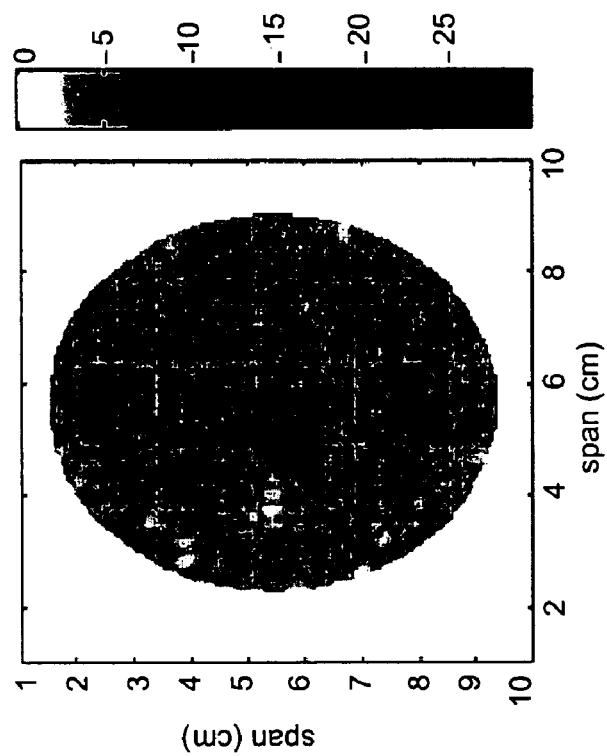
FIG. 12 depicts an image of the scattered energy of the breast using a dB scale when the dielectric properties estimated using the time domain inverse scattering technique in accordance with the invention have been increased by 10%.
Figure 11:
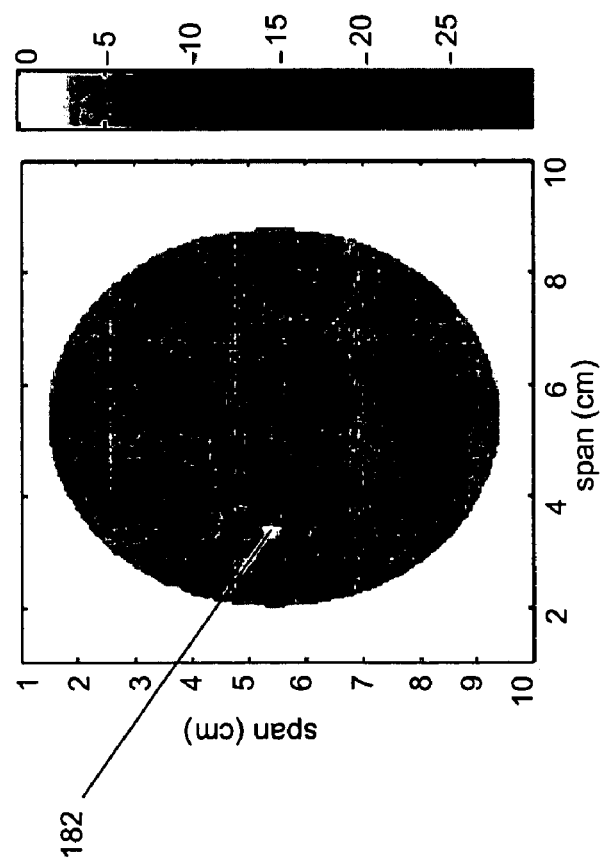
FIG. 11 depicts an image of the scattered energy of the breast using a dB scale when the dielectric properties of a non-dispersive medium are estimated using the time domain inverse scattering technique in accordance with the invention.

To demonstrate the effect of accurate estimated material parameters on the resulting image formation to detect and to locate tumors, a microwave imaging technique described in E. J. Bond, et al., "Microwave Imaging Via Space-Time Beamforming for Early Detection of Breast Cancer," IEEE Trans. Antennas and Propagation, Vol. 51, No. 8, August 2003 was used. See also U.S. published patent application 2003/0088180 A1, "Space-Time Microwave Imaging for Cancer Detection," published May 8, 2003, the disclosure of which is incorporated herein by reference. FIG. 11 shows the results of the image formation using the best estimate of the material parameters for a non-dispersive medium assuming a 2 mm skin thickness. The breast tumor 182 is clearly discernible. FIG. 12 shows the results of the image formation using the best estimate of the material parameters increased by 10%. No breast tumor can be confidently detected in this image due to the high levels of energy that appear throughout the image. This example illustrates that the average properties estimation algorithm results in significantly better detection performance than does reasonable, but incorrect guessing.

Figure 13:
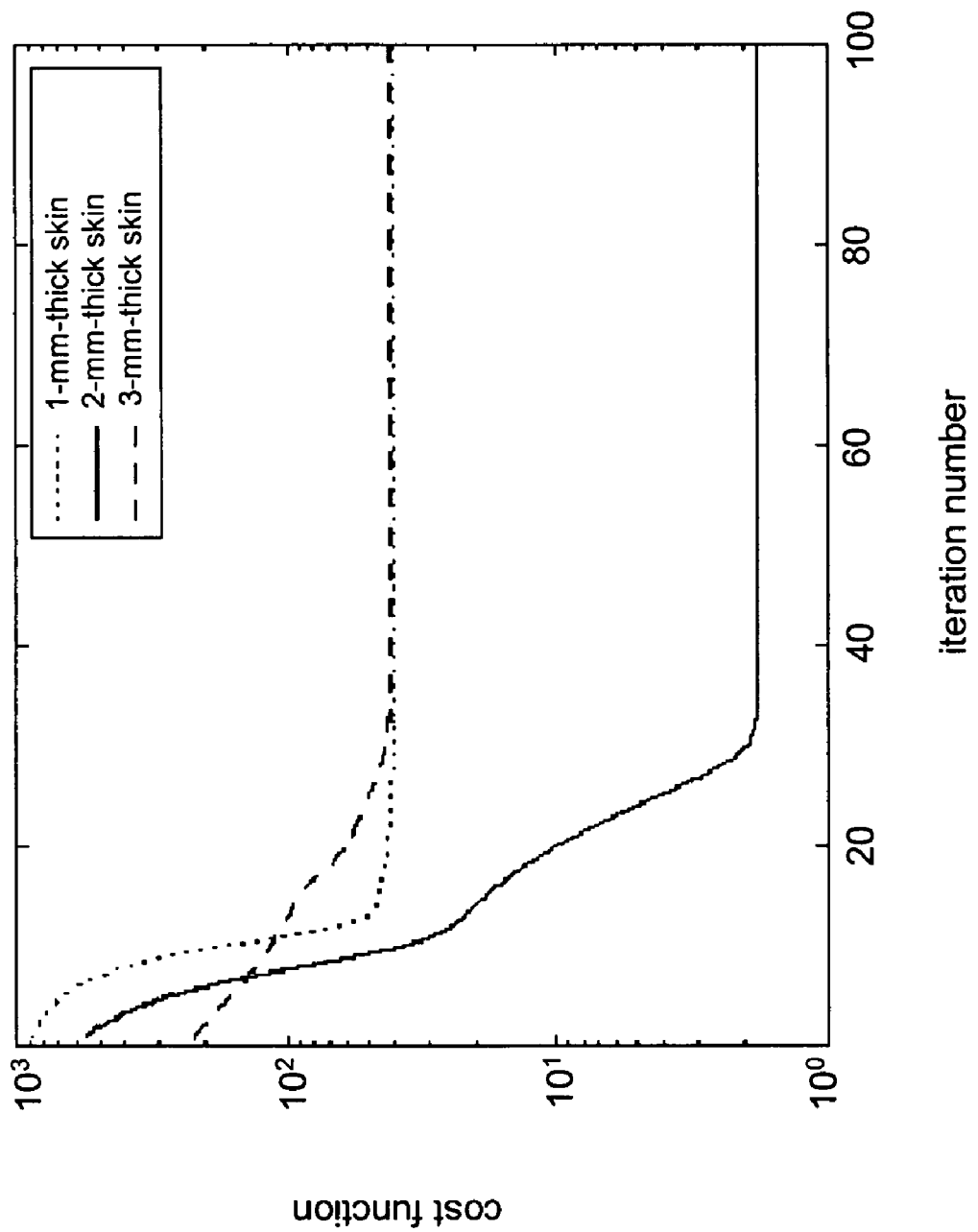
FIG. 13 depicts the cost function as a function of the iteration number for different assumed skin thicknesses wherein the cost function is calculated using the time domain inverse scattering technique in accordance with the invention assuming a dispersive medium.
Figure 14:
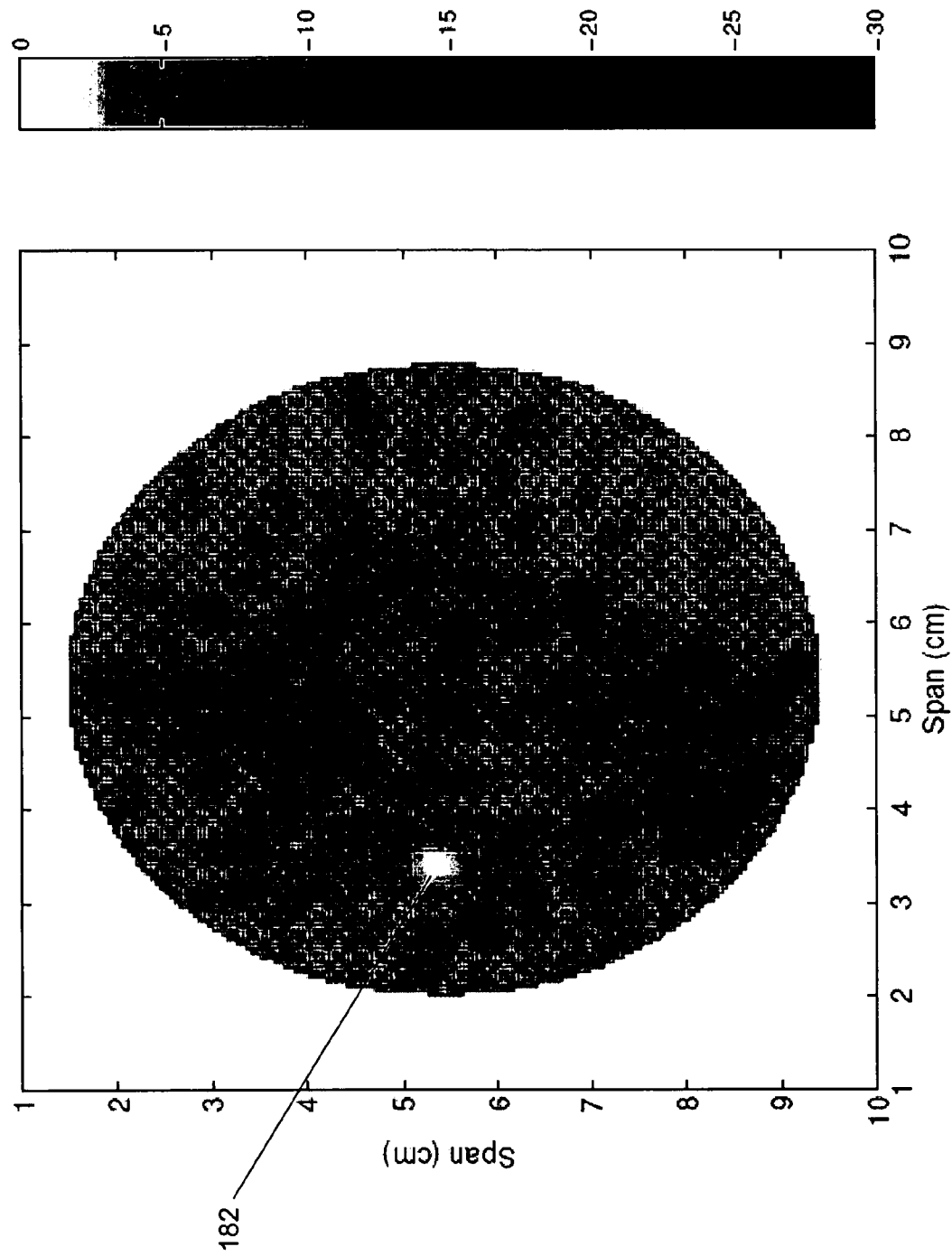
FIG. 14 depicts an image of the scattered energy of the breast using a dB scale when the dielectric properties of a dispersive medium are estimated using the time domain inverse scattering technique in accordance with the invention.

FIG. 13 shows similar results for three different skin thicknesses, 1 mm, 2 mm, and 3 mm, assuming a dispersive medium. FIG. 14 shows the results of the image formation using the best estimate of the material parameters for the dispersive medium that were identified assuming a 2 mm skin thickness. The breast tumor 182 is clearly discernible.

The foregoing description of exemplary embodiments of the invention have been presented for purposes of illustration and of description. It is not intended to be exhaustive or to limit the invention to the precise form disclosed, and modifications and variations are possible in light of the above teachings or may be acquired from practice of the invention. The exemplary embodiments (which can be practiced separately or in combination) were chosen and described in order to explain the principles of the invention and as practical applications of the invention to enable one skilled in the art to utilize the invention in various embodiments and with various modifications as suited to the particular use contemplated. The functionality described may be implemented in a single executable or application or may be distributed among different modules without deviating from the spirit of the invention. Additionally, the order of execution of the operations described may be changed without deviating from the spirit of the invention. It is intended that the scope of the invention be defined by the claims appended hereto and their equivalents. Thus, the description of the preferred embodiments is for purposes of illustration and not limitation.

What is claimed is:

1. A system comprising:
   a plurality of receive antennas configured to receive scattered signals from a target object;
   a receiver coupled to the plurality of receive antennas, the receiver processing the received scattered signals thereby forming measured field data;
   a memory coupled to the receiver, the memory configured to store the measured field data; and
   a processor, the processor coupled to the memory and programmed
   (a) to access the measured field data;
   (b) to define a plurality of regions from the target object;
   (c) to initialize estimation method parameters;
   (d) to calculate field data for each of the plurality of antennas using the estimation method parameters; and
   (e) to estimate a value for each material parameter of a material parameter set using a conjugate-gradient method to minimize a cost function, the cost function measuring the difference between the measured field data and the calculated field data at each of the plurality of antennas wherein the material parameter set includes a material parameter associated with each of the plurality of regions, and further wherein the conjugate-gradient method includes an average gradient calculated for each of the plurality of regions from a gradient calculated at a plurality of points within each of the plurality of regions.

2. The system of claim 1, wherein the estimation method parameters are selected from the group consisting of the material parameter set, a step size set, a memory parameter, and a step size adjustment parameter.

3. The system of claim 1, wherein the plurality of regions comprise a first region and a second region, wherein the first region is a skin layer and the second region is a breast tissue region.

4. The system of claim 1, wherein the processor is further programmed to repeat (b)-(e) for a plurality of target object region definitions and to select a best estimate from the material parameter sets estimated in (e) based on the cost function.

5. The system of claim 1, wherein the material parameter is selected from the group consisting of conductivity, permittivity, permeability, permittivity at infinite frequency, static permittivity, and static conductivity.

6. The system of claim 1, wherein the cost function is evaluated using a cost function gradient defined for the material parameter.

7. The system of claim 1, wherein the conjugate-gradient method includes updating the material parameter based on the equation $p_{n+1}=p_n+\alpha_i(n)\,d_n$, where n is the iteration number, $p_n$ is the value of the material parameter at the $n^{th}$ iteration, $\alpha_i(n)$ is the step size of the $i^{th}$ material parameter of the material parameter set at the $n^{th}$ iteration, and $$d_n = \begin{cases} -g_n & \text{if } n = 1, \\ \beta_n d_{n-1} - g_n & \text{if } n > 1, \end{cases}$$

where $\beta_n$ is a memory parameter at the $n^{th}$ iteration, and $g_n$ is a cost function gradient defined for the material parameter at the $n^{th}$ iteration, and further wherein the $\alpha_i(n)$ for each material parameter of the material parameter set is independent.

8. The system of claim 7, wherein a step size combination includes the step size for each material parameter of the material parameter set, and further wherein the cost function is calculated for each of a plurality of step size combinations.

9. The system of claim 8, wherein each step size value of the plurality of step size is chosen to be either zero or $R_i(n)$, where $R_i(n)$ is an adjustment parameter equation that is a function of the iteration number and that evaluates to a value greater than zero.

10. The system of claim 9, wherein estimating the material parameter set includes updating each material parameter of the material parameter set and selecting the update of the material parameter set that provides a minimum for the cost function.

11. The system of claim 9, wherein $R_i(n)$ is calculated using the equation $$R_i(n) = \begin{cases} 0.85 R_i(n-1) & \text{if } \alpha_i(n-1) = 0 \\ 1.15 R_i(n-1) & \text{if } \alpha_i(n-1) > 0 \end{cases}.$$

12. The system of claim 7, wherein estimating the material parameter set includes updating each material parameter of the material parameter set until a minimization criteria is satisfied.

13. The system of claim 1, wherein calculating the field data is based on Maxwell's equations for a dispersive electromagnetic medium.

14. The system of claim 1, further comprising:
a transmit antenna to transmit a microwave signal toward the target object to be imaged; and
a microwave source connected to the transmit antenna to provide electromagnetic signals to the transmit antenna.

15. A non-transitory computer-readable memory having computer-readable instructions stored thereon that, if executed by a computing device, cause the computing device to perform a process comprising:
receiving measured field data, the field data received by at least one antenna and measured from signals scattered by a target object to be imaged;
defining a plurality of regions from the target object;
initialize estimation method parameters;
calculating field data for each antenna using the estimation method parameters; and
estimating a value for each material parameter of a material parameter set using a conjugate-gradient method to minimize a cost function, the cost function measuring the difference between the measured field data and the calculated field data at each of the plurality of antennas, wherein the material parameter set includes a material parameter associated with each of the plurality of regions, and further wherein the conjugate-gradient method includes an average gradient calculated for each of the plurality of regions from a gradient calculated at a plurality of points within each of the plurality of regions, wherein the estimated material parameter set is configured for use in forming an image of the target object.

16. A method comprising:
(a) receiving measured field data, the field data received by at least one antenna and measured from signals scattered by a target object to be imaged;
(b) defining a plurality of regions from the target object;
(c) initializing estimation method parameters;
(d) calculating field data for each antenna using the estimation method parameters; and
(e) estimating a value for each material parameter of a material parameter set using a conjugate-gradient method to minimize a cost function, the cost function measuring the difference between the measured field data and the calculated field data at each antenna, wherein the material parameter set includes a material parameter associated with each of the plurality of regions, and further wherein the conjugate-gradient method includes an average gradient calculated for each of the plurality of regions from a gradient calculated at a plurality of points within each of the plurality of regions, wherein the estimated material parameter set is configured for use in forming an image of the target object.

17. The method of claim 16, wherein the estimation method parameters are selected from the group consisting of the material parameter set, a step size set, a memory parameter, and a step size adjustment parameter.

18. The method of claim 16, wherein the plurality of regions comprise a first region and a second region, wherein the first region is a skin layer and the second region is a breast tissue region.

19. The method of claim 16, further comprising repeating (b)-(e) for a plurality of target object region definitions and selecting a best estimate from the material parameter sets estimated in (e) based on the cost function.

20. The method of claim 16, wherein the material parameter is selected from the group consisting of conductivity, permittivity, permeability, permittivity at infinite frequency, static permittivity, and static conductivity.

21. The method of claim 16, wherein the cost function is evaluated using a cost function gradient defined for the material parameter.

22. The method of claim 21, wherein the conjugate-gradient method includes updating the material parameter based on the equation $p_{n+1}=p_n+\alpha_i(n)\,d_n$, where n is the iteration number, $p_n$ is the value of the material parameter at the $n^{th}$ iteration, $\alpha_i(n)$ is the step size of the $i^{th}$ material parameter of the material parameter set at the $n^{th}$ iteration, and $$d_n = \begin{cases} -g_n & \text{if } n = 1, \\ \beta_n d_{n-1} - g_n & \text{if } n > 1, \end{cases}$$

where $\beta_n$ is a memory parameter at the $n^{th}$ iteration, and $g_g$ is a cost function gradient defined for the material parameter at the $n^{th}$ iteration, and further wherein the $\alpha_i(n)$ for each material parameter of the material parameter set is independent.

23. The method of claim 22, wherein a step size combination includes the step size for each material parameter of the material parameter set, and further wherein the cost function is calculated for each of a plurality of step size combinations.

24. The method of claim 23, wherein each step size value of the plurality of step size is chosen to be either zero or $R_i(n)$, where $R_i(n)$ is an adjustment parameter equation that is a function of the iteration number and that evaluates to a value greater than zero.

25. The method of claim 24, wherein estimating the material parameter set includes updating each material parameter of the material parameter set and selecting the update of the material parameter set that provides a minimum for the cost function.

26. The method of claim 24, wherein $R_i(n)$ is calculated using the equation $$R_i(n) = \begin{cases} 0.85 R_i(n-1) & \text{if } \alpha_i(n-1) = 0 \\ 1.15 R_i(n-1) & \text{if } \alpha_i(n-1) > 0 \end{cases}.$$

27. The method of claim 22, wherein estimating the material parameter set includes updating each material parameter of the material parameter set until a minimization criteria is satisfied.

28. The method of claim 16, wherein calculating the field data is based on Maxwell's equations for a dispersive electromagnetic medium.

29. A microwave imaging system, the system comprising:
   a transmit antenna configured to transmit a microwave signal toward a target object to be imaged;
   a microwave source connected to the transmit antenna and configured to provide electromagnetic signals to the transmit antenna;
   a plurality of receive antennas configured to receive scattered signals from the target object;
   a receiver coupled to the plurality of receive antennas, the receiver processing the received scattered signals thereby forming measured field data;
   a memory coupled to the receiver, the memory configured to store the measured field data; and
   a processor, the processor coupled to the memory and programmed
      to access the measured field data;
      to define a plurality of regions from the target object;
      to initialize estimation method parameters;
      to calculate field data for each of the plurality of antennas using the estimation method parameters;
      to estimate a value for each material parameter of a material parameter set using a conjugate-gradient method to minimize a cost function, the cost function measuring the difference between the measured field data and the calculated field data at each of the plurality of receive antennas, wherein the material parameter set includes a material parameter associated with each of the plurality of regions, and further wherein the conjugate-gradient method includes an average gradient calculated for each of the plurality of regions from a gradient calculated at a plurality of points within each of the plurality of regions; and
      to create an image of the target object using the estimated material parameter for each of the plurality of regions.

* * * * *